(12) United States Patent
Jeske et al.

(10) Patent No.: US 8,067,407 B2
(45) Date of Patent: Nov. 29, 2011

(54) SUBSTITUTED DIHYDROPYRAZOLONES AND THEIR USE

(75) Inventors: Mario Jeske, Solingen (DE); Ingo Flamme, Reichshof (DE); Friederike Stoll, Düsseldorf (DE); Hartmut Beck, Köln (DE); Metin Akbaba, Ratingen (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 12/427,749

(22) Filed: Apr. 22, 2009

(65) Prior Publication Data

US 2009/0269420 A1 Oct. 29, 2009

(30) Foreign Application Priority Data

Apr. 23, 2008 (DE) .......................... 10 2008 020 113

(51) Int. Cl.
| C07D 401/14 | (2006.01) |
| C07D 403/14 | (2006.01) |
| A61K 31/435 | (2006.01) |
| A61K 31/495 | (2006.01) |

(52) U.S. Cl. .......... 514/211.15; 514/228.8; 514/252.19; 514/256; 540/544; 544/63; 544/295; 544/328

(58) Field of Classification Search ........... 540/544; 544/63, 295, 328; 514/211.15, 228.8, 252.19, 514/256
See application file for complete search history.

(56) References Cited

U.S. PATENT DOCUMENTS

| 4,075,003 | A | 2/1978 | Beck et al. |
| 4,118,574 | A | 10/1978 | Beck et al. |
| 4,663,327 | A | 5/1987 | Sasse et al. |
| 4,698,344 | A | 10/1987 | Sasse et al. |
| 4,806,540 | A | 2/1989 | Sasse et al. |
| 2003/0083351 | A1 | 5/2003 | Almstead et al. |
| 2006/0067927 | A1 | 3/2006 | Chandrasekaran et al. |
| 2006/0160826 | A1 | 7/2006 | Ghanbari et al. |

FOREIGN PATENT DOCUMENTS

| AU | 200029165 | 11/2000 |
| CA | 2364908 A1 | 9/2000 |
| CA | 2608099 A1 | 11/2006 |
| CA | 2667392 | 5/2008 |
| DE | 2651008 A1 | 6/1977 |
| EP | 165448 A2 | 12/1985 |
| EP | 183159 A2 | 6/1986 |
| EP | 212281 A1 | 3/1987 |
| WO | WO-96/12706 A1 | 5/1996 |
| WO | WO-00/51989 A1 | 9/2000 |
| WO | 0292573 A2 | 11/2002 |
| WO | WO-03/051833 A2 | 6/2003 |
| WO | WO-03/074550 A2 | 9/2003 |
| WO | 2004052284 | 6/2004 |
| WO | 2004087066 | 10/2004 |
| WO | WO-2004/089303 A2 | 10/2004 |
| WO | 2005030121 | 4/2005 |
| WO | WO-2006/101903 A1 | 9/2006 |
| WO | 2006114213 | 11/2006 |
| WO | WO-2006/114213 A1 | 11/2006 |
| WO | WO-2007/008541 A2 | 1/2007 |
| WO | 2008049538 | 5/2008 |
| WO | 2008067871 | 6/2008 |
| WO | 2008067874 | 6/2008 |
| WO | WO-2008/067871 A1 | 6/2008 |

OTHER PUBLICATIONS

Vippagunta et al., Crystalline Solids, Advanced Drug Delivery Reviews, 48, pp. 3-26, 2001.*
West, Solid Solutions, Chapter 10, pp. 358 and 365, 1988.*
Ulrich, Crystallization: 4. Crystal Characteristics, Kirk-Othmer Encyclopedia of Chemical Technology, Aug. 2002.*
G. Eder: "Allgemeine Pathologie und Pathologische Anatomie," Aufl, Springer Verlag, Berlin, vol. 33, 1990.
R. F. Schmidt et al.: "Physiologie des Menschen," Aufl, Springer Verlag, Berlin, vol. 27, 1997.
G. Löffler et al: "Biochemie und Pathobiochemie," Aufl, Springer Verlag, Berlin, vol. 7, 2003, pp. 1-22.
M. Simons et al.: "Therapeutic Angiogenesis in Cardiovascular Disease," Nat. Rev. Drug. Discov., vol. 2, No. 11, 2003, pp. 863-871.
K.-U. Eckardt: "The Potential of Erythropoietin and Related Strategies to Stimulate Erythropoiesis," Current Opinion in Investigational Drugs, vol. 2, No. 8, 2001, pp. 1081-1085.
J. S. Berns: "Should the Target Hemoglobin for Patients with Chronic Kidney Disease Treated with Erythropoietic Replacement Therapy be Changed?" Seminars in Dialysis, vol. 18, No. 1, Jan.-Feb. 2005, pp. 22-29.
K. Caiola et al.: "Use of Erythropoietin in Heart Failure Management," The Annals of Pharmacotherapy, vol. 38, Dec. 2004, pp. 2145-2149.
S. D. Katz: "Mechanisms and Treatment of Anemia in Chronic Heart Failure," Cong. Heart Failure, vol. 10, 2004, pp. 243-247.
G. L. Semenza: "Hypoxia-Inducible Factor 1: Oxygen Homeostasis and Disease Pathophysiology," Trends in Molecular Medicine, vol. 7, No. 8, Aug. 2001, pp. 345-350.
R. H. Wenger et al.: "Oxygen(es) and the Hypoxia-Inducible Factor-1," Biol. Chem., vol. 378, Jul. 1997, pp. 609-616.
A. C. R. Epstein et al.: "*C. elegans* EGL-9 and Mammalian Homologs Define a Family of Dioxygenases that Regulate HIF by Prolyl Hydroxylation," Cell, vol. 107, Oct. 5, 2001, pp. 43-54.
R. K. Bruick et al.: "A Conserved Family of Prolyl-4-Hydroxylases that Modify HIF," Science 294, Nov. 9, 2001, pp. 1337-1340.
M. Ivan et al.: "Biochemical Purification and Pharmacological Inhibition of a Mammalian Prolyl Hydroxylase Acting on Hypoxia-Inducible Factor," Proc. Natl. Acad. Sci., vol. 99, No. 21, Oct. 15, 2002, pp. 13459-13464.
L. Aravind et al.: "The DNA-Repair Protein AlkB, EGL-9, and Leprecan Define New Families of 2-Oxoglutarate- and Iron-Dependent Dixygenases," Genome Biology, vol. 2, No. 3, Feb. 19, 2001, pp. 1-8.

(Continued)

*Primary Examiner* — Deepak Rao

(57) ABSTRACT

The present application relates to novel substituted dihydropyrazolone derivatives, processes for their preparation, their use for treatment and/or prophylaxis of diseases and their use for the preparation of medicaments for treatment and/or prophylaxis of diseases, in particular cardiovascular and haematological diseases and kidney diseases, and for promoting wound healing.

21 Claims, No Drawings

OTHER PUBLICATIONS

C. J. Schofield et al.: "Oxygen Sensing by HIF Hydroxylases," Nature Reviews Molecular Cell Biology, vol. 5, May 2004, pp. 343-354.

J. Büchi et al.: "Synthese and Pharmakologische Eigenschaften Einiger Pyridyl-Pyrazol-5-one," Helv. Chim. Acta, vol. 49, No. 1, 1966, pp. 272-280.

B. Djerrari et al.: "3-Methyl-1-(Pyridin-2-yl)-4-(1-Pyridin-2-yl-3-Methyl-1*H*-Pyrazol-5-yl)-2*H*-3-Pyrazolin-5(1*HI*)-one," Acta Crystallographica Section E, Structure Reports Online, E57, No. 11, 2001, o1126-o1127.

S. P. Singh et al.: "Reaction of 1-[5-Hydroxy-3-Methyl-1-(2-Thiazolyl)-4-Pyrazolyl]-1,3-Butanediones with Phenyl and Heterocyclic Hydrazines: a Convenient Synthesis of 4,5-Bipyrazoles," Indian Journal of Heterocyclic Chemistry, vol. 3, Jul.-Sep. 1993, pp. 5-8.

J. Elguero et al.: "A 1H and 13C NMR Study of the Structure and Tautomerism of 4-Pyrazolylpyrazolinones," J. Heterocyclic Chem., vol. 37, No. 4, May-Jun. 1990, pp. 865-870.

H. Barth et al.: "Konstitution and Synthese des Muscafavins," Liebigs Ann. Chem., 1981, pp. 2164-2179.

R.A. Evans et al.—Trifluromethyl-substituted Dehydrodizepines and Cyanopyrroles form Azido-ffetrazolo-pyridines, J Chem. Commun., vol. 15, 1992, pp. 1062-1064.

F. Oehme et al.: "A Nonradioactive 96-well Plate Assay for the Detection of Hypozia-Inducible Factor Prolyl Hydroxylase Activity," Analytical Biochemistry, vol. 330, 2004, pp. 74-80.

F. Oehme et al.: "Overexpression of Ph-4, a Novel Putative Proline 4-Hydroxylase, Modulates Activity of Hypoxia-Inducible Transcription Factors," Biochemical and Biophysical Research Communications, vol. 296, 2002, pp. 343-349.

C. A. Heid et al.: "Real Time Quantitative PCR," Genome Research, vol. 6, No. 10, 1996, pp. 986-994.

N. Yokoyama et al.: "Synthesis and Structure-Activity Relationships of Oxamic Acid and Acetic Acid Derivatives Related to L-Thyronine," J. Med. Chem. vol. 38, 1995, pp. 695-707.

N. Sperber et al.: "Parasympathetic Blocking Agents, III. N-Alkylpiperidinecarboxylic Esters," J. Am. Chem. Soc. vol. 81, 1959, pp. 704-709.

M. A. Meziane et al.: "A New Route to 1-Oxo-1,2-Dihydropyrimido[1,6-a]Benzimidazole-4-Carboxylates from Ethyl 2-(Benzimidazol-2-yl)-3-(Dimethylamino)Acrylate Using Solvent-Free Conditions," Synthesis, Jul. 1996, pp. 967-969.

U.S. Appl. No. 11/919,478, the US National Stage of International Application No. PCT/EP20061003488 filed on Apr. 15, 2006.

International Search Report for International Application No. PCT/EP2006/003488, published with the International Application as WO2006/114213 on Nov. 2, 2006.

U.S. Appl. No. 12/447,192, the US National Stage of International App. No. PCT/EP/2007/008977, filed on Oct. 17, 2007.

International Search Report for International App No. PCT/EP/2007/008977, published with the International Application as WO2008/067871 on May 2, 2008.

U.S. Appl. No. 12/447,201, the US National Stage of International App No. PCT/EP/20071008877, filed on Oct. 12, 2007.

International Search Report for International App No. PCT/EP/2007/008877, published with the International Application as WO2008/049538 on Jun. 12, 2008.

U.S. Appl. No. 12/447,207, the US National Stage of International App No. PCT/EP/20071008951, filed on Oct. 16, 2007.

International Search Report for International App No. PCT/EP/2007/008951, published with the International Application as WO2008/067874 on Jun. 12, 2008.

An English translation of WO2006/114213 was published as US Application Publication No. 20100035906 on Feb. 11, 2010. (U.S. Appl. No. 11/919,478).

An English translation of WO2008/067871 was published as US Application Publication No. 20100305085 on Dec. 2, 2010 (U.S. Appl. No. 12/447,192).

An English translation of WO2008/049538 was published as Canadian Application Publication No. CA2667392 on May 2, 2008. (copy of the Canadian publication is cited above and transmitted herewith).

An English translation of WO2008/067874 was published as US Application Publication No. 2010093803 on Apr. 15, 2010.

International Search Report for International Patent App No. PCT/EP20091002693, published with the International Application as WO 2009/129945. The application is an international counterpart of the present application. published Oct. 29, 2009.

R.I. Dowell et al., "Novel Inhibitore of Prolyl 4-hydroxylase: Part 4. Pyridine-2-Carboxylic Acid Analogues with Alternative 2-Substituents," Eur. J. Med. Chem, 1993, 28, pp. 513-516, Elsevier, Paris.

Hill et al. "Inhibition of TRPM2 channels by the antifungal agents clotrimazole and econazole," Naunyn Schmiedebergs Arch. Pharmacol, 2004, vol. 370, pp. 277-238, abstract only.

\* cited by examiner

SUBSTITUTED DIHYDROPYRAZOLONES AND THEIR USE

RELATED APPLICATIONS/PATENTS AND INCORPORATION BY REFERENCE

This application claims priority to German Patent Application Number 102008020113.8 filed on Apr. 23, 2008, the contents of which are hereby incorporated by reference.

The foregoing application, and all documents cited therein, and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

BACKGROUND

1. Field of the Invention

The present application relates to novel substituted dihydropyrazolone derivatives, processes for their preparation, their use for treatment and/or prophylaxis of diseases and their use for the preparation of medicaments for treatment and/or prophylaxis of diseases, in particular cardiovascular and haematological diseases and kidney diseases, and for promoting wound healing.

2. Background of the Invention

A deficient supply of oxygen to the human organism or its components which either impairs regular functioning of the organism or its components due to its duration and/or its extent or causes its functioning to break down completely is called hypoxia. Hypoxia can be caused by a reduction in the available oxygen in the air breathed in (for example during periods at a high altitude), by disorders in external respiration (for example as a result of disturbed functioning of the lungs or obstruction of the respiratory tract), by a reduction in the cardiac output (for example in the event of cardiac insufficiency, acute right ventricular overloading with pulmonary embolism), by too low an oxygen transport capacity of the blood (for example as a result of an anaemia or intoxication, for example with carbon monoxide), locally demarcated by a reduced blood flow as a result of vascular occlusions (ischaemia states typically for example of the heart, the lower extremities or the brain, diabetic macro- and microangiopathy) or also by an increased oxygen requirement of the tissue (for example as a result of increased muscular activity or local inflammations) [Eder, Gedigk (ed.), *Allgemeine Pathologie und pathologische Anatomie*, 33rd ed., Springer Verlag, Berlin, 1990]

The human organism is capable to a limited extent of adapting acutely and chronically to situations of reduced oxygen supply. In addition to an immediate response, which includes inter alia an increase in the cardiac output and respiratory output and a local dilation of blood vessels by vegetative-nervous control mechanisms, hypoxia brings about a change in the transcription of numerous genes. The function of the gene products here serves to compensate the oxygen deficiency. Thus, expression of several enzymes of glycolysis and glucose transporter 1 is enhanced, as a result of which anaerobic ATP production increases and survival of the oxygen deficiency is rendered possible [Schmidt, Thews (ed.), *Physiologie des Menschen*, 27th ed., Springer Verlag, Berlin, 1997; Löffler, Petrides (ed.), *Biochemie und Pathobiochemie*, 7th ed., Springer Verlag, Berlin, 2003].

Hypoxia furthermore leads to enhanced expression of vascular endothelial cell growth factor, VEGF, as a result of which regeneration of blood vessels (angiogenesis) is stimulated in hypoxic tissues. The blood flow through ischaemic tissue is thereby improved in the long term. This counter-regulation is evidently only very inadequate in the case of various cardiovascular diseases and vascular occlusion diseases [overview in: Simons and Ware, *Therapeutic angiogenesis in cardiovascular disease*, Nat. Rev. Drug. Discov. 2 (11), 863-71 (2003)].

Furthermore, in cases of systemic hypoxia expression of the peptide hormone erythropoietin formed predominantly in the interstitial fibroblasts of the kidneys is enhanced. The formation of red blood cells in the bone marrow is thereby stimulated, and the oxygen transport capacity of the blood is therefore increased. This effect has been and is used by high-performance athletes in so-called high altitude training. A decrease in the oxygen transport capacity of the blood for example as a result of anaemia after hemorrhaging usually causes an increase in erythropoietin production in the kidney. With certain forms of anaemia, this regulatory mechanism may be disturbed or its normal value may be set lower. Thus for example in patients suffering from renal insufficiency, erythropoietin is indeed produced in the kidney parenchyma, but in significantly reduced amounts with respect to the oxygen transport capacity of the blood, which results in so-called renal anaemia. Renal anaemia in particular, but also anemias caused by tumours and HIV infection are conventionally treated by parenteral administration of recombinant human erythropoietin (rhEPO). No alternative therapy with an orally available medicament currently exists for this expensive therapy [overview in: Eckardt, *The potential of erythropoietin and related strategies to stimulate erythropoiesis*, Curr. Opin. Investig. Drugs 2(8), 1081-5 (2001); Berns, *Should the target hemoglobin for patients with chronic kidney disease treated with erythropoietic replacement therapy be changed?*, Semin. Dial. 18 (1), 22-9 (2005)]. Recent studies demonstrate that, in addition to its erythropoiesis-increasing action, erythropoietin also has a protective (anti-apoptotic) action, which is independent thereof, on hypoxic tissue, in particular the heart and the brain.

Furthermore, according to recent studies therapy with erythropoietin reduces the average severity of morbidity in patients with cardiac insufficiency [overviews in: Caiola and Cheng, *Use of erythropoietin in heart failure management*, Ann. Pharmacother. 38 (12), 2145-9 (2004); Katz, *Mechanisms and treatment of anemia in chronic heart failure*, Congest. Heart. Fail. 10 (5), 243-7 (2004)].

The genes described above which are induced by hypoxia have the common feature that the increase in their expression under hypoxia is caused by the so-called hypoxia-inducible transcription factor (HIF). HIF is a heterodimeric transcription factor which comprises an alpha and a beta subunit. Three HIF alpha isoforms have been described, of which HIF-1 alpha and HIF-2 alpha are highly homologous and are of importance for hypoxia-induced gene expression. While the beta subunit (of which 2 isoforms have been described), which is also called ARNT (aryl hydrocarbon receptor nuclear translocator), is expressed constitutively, expression of the alpha subunit depends on the oxygen content in the cell. Under normoxia, the HIF alpha protein is poly-ubiquitinized and then degraded proteasomally. Under hypoxia this degradation is inhibited, so that HIF alpha dimerizes with ARNT and can activate its target genes. The HIF dimer bonds here to so-called hypoxia-responsible elements (HRE) in the regulatory sequences of its target genes. The HRE are defined by a consensus sequence. Functional HRE have been detected in the regulatory elements of numerous hypoxia-induced genes [overviews in: Semenza, *Hypoxia-inducible factor 1: oxygen*

*homeostasis and disease pathophysiology*, Trends Mol. Med. 7 (8), 345-50 (2001); Wenger and Gassmann, *Oxygen(es) and the hypoxia-inducible factor-1*, Biol. Chem. 378 (7), 609-16 (1997)].

The molecular mechanism on which this regulation of HIF alpha is based has been clarified by the works of several independent groups of researchers. The mechanism is conserved from species to species: HIF alpha is hydroxylated by a subclass of oxygen-dependent prolyl 4-hydroxylases, called PHD or EGLN, on two specific prolyl radicals (P402 and P564 of the human HIF-1 alpha subunit). The HIF prolyl 4-hydroxylases are iron-dependent, 2-oxoglutarate-converting dioxygenases [Epstein et al., *C. elegans EGL-9 and mammalian homologs define a family of dioxygenases that regulate HIF by prolyl hydroxylation*, Cell 107 (1), 43-54 (2001); Bruick and McKnight, *A conserved family of prolyl-4-hydroxylases that modify HIF*, Science 294 (5545), 1337-40 (2001); Ivan et al., *Biochemical purification and pharmacological inhibition of a mammalian prolyl hydroxylase acting on hypoxia-inducible factor*, Proc. Natl. Acad. Sci. U.S.A. 99 (21), 13459-64 (2002)]. The enzymes were annotated as prolyl hydroxylases for the first time in 2001 [Aravind and Koonin, *The DNA-repair protein AlkB, EGL-9, and leprecan define new families of 2-oxoglutarate- and iron-dependent dioxygenases*, Genome Biol. 2 (3), research0007.1-0007.8, Epub 2001 Feb. 19].

The pVHL tumour suppressor protein, which together with elongin B and C forms the so-called VBC complex, which adapts the HIF alpha subunit to an E3 ubiquitin ligase, bonds to the prolyl-hydroxylated HIF alpha subunit. Since the prolyl 4-hydroxylation of the HIF alpha subunit and its subsequent degradation takes place as a function of the intracellular concentration of oxygen, HIF prolyl 4-hydroxylases have also been called a cellular oxygen sensor. Three isoforms of these enzymes have been identified: EGLN1/PHD2, EGLN2/PHD1 and EGLN3/PHD3. Two of these enzymes (EGLN2/PHD1 and EGLN3/PHD3) are induced transcriptionally even under hypoxia and are possibly responsible for the lowering of the HIF alpha levels to be observed under chronic hypoxia [overview in: Schofield and Ratcliffe, *Oxygen sensing by HIF hydroxylases*, Nat. Rev. Mol. Cell. Biol. 5 (5), 343-54 (2004)].

Selective pharmacological inhibition of HIF prolyl 4-hydroxylases brings about the increase in the gene expression of HIF-dependent target genes and is therefore beneficial for the therapy of numerous disease syndromes. In the case of diseases of the cardiovascular system in particular, an improvement in the course of the diseases is to be expected from induction of new blood vessels and the change in the metabolic situation of ischaemic organs from aerobic to anaerobic ATP production. An improvement in the vascularization of chronic wounds promotes the healing process, especially in the case of poorly healing ulcera cruris and other chronic skin wounds. The induction of endogenous erythropoietin in certain disease forms, in particular in patients with renal anaemia, is likewise a therapeutic goal to be aimed for.

The HIF prolyl 4-hydroxylase inhibitors described hitherto in the scientific literature do not meet the requirements to be imposed on a medicament. These are either competitive oxoglutarate analogues (such as for example N-oxalylglycine), which are characterized by their very low action potency, and therefore in in vivo models have as yet shown no action in the sense of an induction of HIF target genes. Or they are iron-complexing agents (chelators), such as desferroxamine, which act as non-specific inhibitors of iron-containing dioxygenases and, although they bring about an induction of the target genes, such as for example erythropoietin, in vivo, evidently counteract erythropoiesis by complexing of the available iron.

2-Heteroaryl-4-aryl-1,2-dihydropyrazolones having a bactericidal and/or fungicidal action are disclosed in EP 165 448 and EP 212 281. The use of 2-heteroaryl-4-aryl-1,2-dihydropyrazolones as lipoxygenase inhibitors for treatment of respiratory tract, cardiovascular and inflammatory diseases is claimed in EP 183 159. 2,4-Diphenyl-1,2-dihydropyrazolones having a herbicidal activity are described in DE 2 651 008. The preparation and pharmacological properties of certain 2-pyridyl-1,2-dihydropyrazolones are reported in *Helv. Chim. Acta* 49 (1), 272-280 (1966). WO 96/12706, WO 00/51989 and WO 03/074550 claim compounds having a dihydropyrazolone partial structure for treatment of various diseases, and hydroxy- or alkoxy-substituted bipyrazoles for treatment of neuropsychiatric diseases are disclosed in WO 2006/101903. Heteroaryl-substituted pyrazole derivatives for treatment of pain and various CNS diseases are furthermore described in WO 03/051833 and WO 2004/089303. WO 2006/114213 has meanwhile disclosed 2,4-dipyridyl-1,2-dihydropyrazolones as inhibitors of HIF prolyl 4-hydroxylases.

The X-ray crystal structure of the compound 3-methyl-1-(pyridin-2-yl)-4-(1-pyridin-2-yl-3-methyl-1H-pyrazol-5-yl)-2H-3-pyrazolin-5(1H)-one (other name: 5,5'-dimethyl-2,2'-dipyridin-2-yl-1',2'-dihydro-2H,3'H-3,4'-bipyrazol-3'-one) is reported in *Acta Crystallogr., Section E: Structure Reports Online* E57 (11), o1126-o1127 (2001) [*Chem. Abstr.* 2001:796190]. The synthesis of certain 3',5-dimethyl-2-phenyl-1'-(1,3-thiazol-2-yl)-1'H,2H-3,4'-bipyrazol-5'-ol derivatives is described in *Indian J. Heterocyclic Chem.* 3 (1), 5-8 (1993) [*Chem. Abstr.* 1994:323362]. The preparation and tautomerism of individual 4-(pyrazol-5-yl)pyrazolin-5-one derivatives is reported in *J. Heterocyclic Chem.* 27 (4), 865-870 (1990) [*Chem. Abstr.* 1991:428557]. A therapeutic use has not hitherto been described for the compounds mentioned in these publications. The compound 2-tert-butyl-1'-[4-(4-chlorophenyl)-1,3-thiazol-2-yl]-3',5-dimethyl-1'H,2H-3,4'-bipyrazol-5'-ol is listed as a test example in WO 2007/008541.

SUMMARY

An object of the present invention is to provide novel compounds which can be employed for treatment of diseases, in particular cardiovascular and haematological diseases.

In the context of the present invention, compounds are now described which act as specific inhibitors of HIF prolyl 4-hydroxylases and on the basis of this specific action mechanism bring about in vivo, after parenteral or oral administration, the induction of HIF target genes, such as e.g. erythropoietin, and the biological processes thereby caused, such as e.g. erythropoiesis.

The present invention provides compounds of the formula

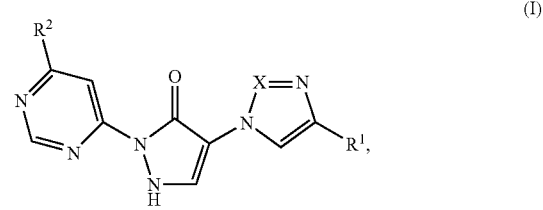

in which

X represents N or CH, $R^1$ represents hydrogen or cyano, $R^2$ represents a saturated 4- to 7-membered heterocyclyl radical which is attached via a nitrogen atom, where the heterocyclyl radical may be substituted by a substituent, where the substituent is selected from the group consisting of hydroxyl, hydroxycarbonyl, $C_1$-$C_3$-alkyl, $C_1$-$C_3$-alkylamino and $C_3$-$C_6$-cycloalkyl, or where the heterocyclyl radical may be substituted by 1 to 4 fluorine substituents, and salts, solvates and solvates of the salts thereof.

DETAILED DESCRIPTION

Compounds according to the invention are the compounds of the formula (I) and their salts, solvates and solvates of the salts, and the compounds included in the formula (I) and mentioned in the following as embodiment examples and their salts, solvates and solvates of the salts, where the compounds included in the formula (I) and mentioned in the following are not already salts, solvates and solvates of the salts.

The compounds according to the invention can exist in stereoisomeric forms (enantiomers, diastereomers), depending on their structure. The invention therefore includes the enantiomers or diastereomers and their particular mixtures. The stereoisomerically uniform constituents can be isolated from such mixtures of enantiomers and/or diastereomers in a known manner.

Where the compounds according to the invention can occur in tautomeric forms, the present invention includes all the tautomeric forms.

Preferred salts in the context of the present invention are physiologically acceptable salts of the compounds according to the invention. Salts which are not themselves suitable for pharmaceutical uses but can be used, for example, for isolation or purification of the compounds according to the invention are also included.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, such as, by way of example and preferably, alkali metal salts (for example sodium and potassium salts), alkaline earth metal salts (for example calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are described as those forms of the compounds according to the invention which form a complex in the solid or liquid state by coordination with solvent molecules. Hydrates are a specific form of solvates, in which the coordination takes place with water. Hydrates are preferred solvates in the context of the present invention.

The present invention moreover also includes prodrugs of the compounds according to the invention. The term "prodrugs" includes compounds which themselves can be biologically active or inactive, but are converted (for example metabolically or hydrolytically) into compounds according to the invention during their dwell time in the body.

In the context of the present invention, the substituents have the following meaning, unless specified otherwise:

Alkyl per se and "alkyl" in alkylamino represent a straight-chain or branched alkyl radical having 1 to 3 carbon atoms, by way of example and by way of preference methyl, ethyl, n-propyl, isopropyl.

Alkylamino represents an alkylamino radical having one or two (selected independently of one another) alkyl substituents, by way of example and by way of preference methylamino, ethylamino, n-propylamino, isopropylamino, N,N-dimethylamino, N,N-diethylamino, N-ethyl-N-methylamino, N-methyl-N-n-propylamino and N-isopropyl-N-n-propylamino. $C_1$-$C_3$-Alkylamino, for example, represents a monoalkylamino radical having 1 to 3 carbon atoms or represents a dialkylamino radical having 1 to 3 carbon atoms each per alkyl substituent.

Cycloalkyl represents a monocyclic cycloalkyl group having generally 3 to 6 carbon atoms; cycloalkyl radicals which may be mentioned by way of example and by way of preference are cyclopropyl, cyclobutyl, cyclopentyl and cyclohexyl.

A saturated 4- to 7-membered heterocyclyl radical which is attached via a nitrogen atom represents a monocyclic saturated heterocyclic radical having 4 to 7 ring atoms which contain one nitrogen atom via which it is attached and up to 2, preferably up to one, further heteroatom(s) and/or a heterogroup selected from the group consisting of N, O, S, SO, $SO_2$, where a nitrogen atom may also form an N-oxide. Preference is given to 4- to 7-membered monocyclic saturated heterocyclyl radicals having up to one further heteroatom from the group consisting of O, N and S, by way of example and by way of preference azetidin-1-yl, pyrrolin-1-yl, piperidin-1-yl, morpholin-4-yl, thiomorpholin-4-yl, piperazin-1-yl, 1,2-oxazinan-2-yl, 1,4-oxazepan-4-yl, 1,4-thiazepan-4-yl.

Preference is given to compounds of the formula (I), in which

X represents N or CH, $R^1$ represents hydrogen or cyano, $R^2$ represents a saturated 4- to 7-membered heterocyclyl radical which is attached via a nitrogen atom, where the heterocyclyl radical is substituted by 1 to 4 fluorine substituents, or $R^2$ represents piperazin-1-yl, where piperazin-1-yl is substituted by one substituent, where the substituent is selected from the group consisting of $C_3$-$C_6$-cycloalkyl, or $R^2$ represents azetidin-1-yl, where azetidin-1-yl is substituted by one substituent, where the substituent is selected from the group consisting of hydroxycarbonyl, $C_1$-$C_3$-alkyl, $C_1$-$C_3$-alkylamino and $C_3$-$C_6$-cycloalkyl, or $R^2$ represents 1,2-oxazinan-2-yl or 1,4-oxazepan-4-yl, and salts, solvates and solvates of the salts thereof.

Preference is given to compounds of the formula (I) in which
X represents N or CH,
$R^1$ represents hydrogen or cyano,
$R^2$ represents azetidin-1-yl, pyrrolin-1-yl or piperidin-1-yl,
  where azetidin-1-yl, pyrrolin-1-yl and piperidin-1-yl are substituted by 1 to 4 fluorine substituents,
or
$R^2$ represents piperazin-1-yl,
  where piperazin-1-yl is substituted in the 4-position by one substituent, where the substituent is selected from the group consisting of $C_3$-$C_6$-cycloalkyl,
or
$R^2$ represents azetidin-1-yl,
  where azetidin-1-yl is substituted in the 3-position by one substituent, where the substituent is selected from the group consisting of hydroxycarbonyl, methyl and dimethylamino,
or
$R^2$ represents 1,2-oxazinan-2-yl or 1,4-oxazepan-4-yl,
and salts, solvates and solvates of the salts thereof.

Preference is also given to compounds of the formula (I) in which
X represents N or CH,
$R^1$ represents hydrogen or cyano,
$R^2$ represents a saturated 4- to 7-membered heterocyclyl radical which is attached via a nitrogen atom,
  where the heterocyclyl radical is substituted by 1 to 4 fluorine substituents,
and salts, solvates and solvates of the salts thereof.

Preference is also given to compounds of the formula (I) in which
X represents N or CH,
$R^1$ represents hydrogen or cyano,
$R^2$ represents azetidin-1-yl, pyrrolin-1-yl or piperidin-1-yl,
  where azetidin-1-yl, pyrrolin-1-yl and piperidin-1-yl are substituted by 1 to 4 fluorine substituents,
and salts, solvates and solvates of the salts thereof.

Preference is also given to compounds of the formula (I) in which
X represents N or CH,
$R^1$ represents hydrogen or cyano,
$R^2$ represents azetidin-1-yl, pyrrolin-1-yl or piperidin-1-yl,
  where azetidin-1-yl, pyrrolin-1-yl and piperidin-1-yl are substituted by 2 fluorine substituents, where these substituents are attached to the same carbon atom,
and salts, solvates and solvates of the salts thereof.

Preference is also given to compounds of the formula (I) in which
X represents N or CH,
$R^1$ represents hydrogen or cyano,
$R^2$ represents piperazin-1-yl,
  where piperazin-1-yl is substituted by one substituent, where the substituent is selected from the group consisting of $C_3$-$C_6$-cycloalkyl,
and salts, solvates and solvates of the salts thereof.

Preference is also given to compounds of the formula (I) in which
X represents N or CH,
$R^1$ represents hydrogen or cyano,
$R^2$ represents piperazin-1-yl,
  where piperazin-1-yl is substituted in the 4-position by one substituent, where the substituent is selected from the group consisting of $C_3$-$C_6$-cycloalkyl,
and salts, solvates and solvates of the salts thereof.

Preference is also given to compounds of the formula (I) in which
X represents N or CH,
$R^1$ represents hydrogen or cyano,
$R^2$ represents azetidin-1-yl,
  where azetidin-1-yl is substituted by one substituent, where the substituent is selected from the group consisting of hydroxycarbonyl, $C_1$-$C_3$-alkyl, $C_1$-$C_3$-alkylamino and $C_3$-$C_6$-cycloalkyl,
and salts, solvates and solvates of the salts thereof.

Preference is also given to compounds of the formula (I) in which
X represents N or CH,
$R^1$ represents hydrogen or cyano,
$R^2$ represents azetidin-1-yl,
  where azetidin-1-yl is substituted by one substituent, where the substituent is selected from the group consisting of hydroxycarbonyl, methyl and dimethylamino,
and salts, solvates and solvates of the salts thereof.

Preference is also given to compounds of the formula (I) in which
X represents N or CH,
$R^1$ represents hydrogen or cyano,
$R^2$ represents azetidin-1-yl,
  where azetidin-1-yl is substituted in the 3-position by one substituent, where the substituent is selected from the group consisting of hydroxycarbonyl, methyl and dimethylamino,
and salts, solvates and solvates of the salts thereof.

Preference is also given to compounds of the formula (I) in which
X represents N or CH,
$R^1$ represents hydrogen or cyano,
$R^2$ represents 1,2-oxazinan-2-yl or 1,4-oxazepan-4-yl.

Preference is also given to compounds of the formula (I) in which X represents N.

Preference is also given to compounds of the formula (I) in which $R^1$ represents hydrogen.

Preference is also given to compounds of the formula (I) in which $R^1$ represents cyano.

Preference is also given to compounds of the formula (I) in which $R^2$ represents 4-cyclobutyl-piperazin-1-yl.

Preference is also given to compounds of the formula (I) in which
X represents N or CH,
$R^1$ represents cyano,
$R^2$ represents a saturated 4- to 7-membered heterocyclyl radical which is attached via a nitrogen atom,
  where the heterocyclyl radical is substituted by one substituent, where the substituent is selected from the group consisting of hydroxy, hydroxycarbonyl, $C_1$-$C_3$-alkyl, $C_1$-$C_3$-alkylamino and $C_3$-$C_6$-cycloalkyl,
  or
  where the heterocyclyl radical is substituted by 1 to 4 fluorine substituents,
and salts, solvates and solvates of the salts thereof.

The radical definitions given in detail in the particular combinations or preferred combinations of radicals are also replaced as desired by radical definitions of other combinations, independently of the particular radical combinations given.

Combinations of two or more of the abovementioned preferred ranges are very particularly preferred.

The 1,2-dihydropyrazol-3-one derivatives of the formula (I) according to the invention can also be in the tautomeric 1H-pyrazol-5-ol form (I') (see following Scheme 1); the two tautomeric forms are expressly included in the present invention.

Scheme 1

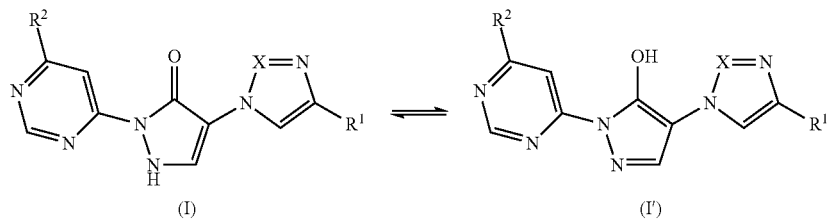

The invention also provides a process for the preparation of the compounds of the formula (I), or salts, solvates and solvates of the salts thereof, wherein, according to process

[A] compounds of the formula

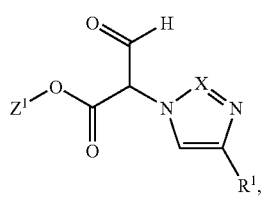

in which $R^1$ has the meaning given above, and
$Z^1$ represents methyl or ethyl,
are reacted in an inert solvent, if appropriate in the presence of an acid, with a compound of the formula

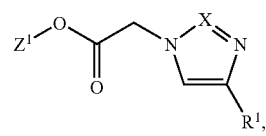

in which R has the meaning given above,
to give compounds of the formula

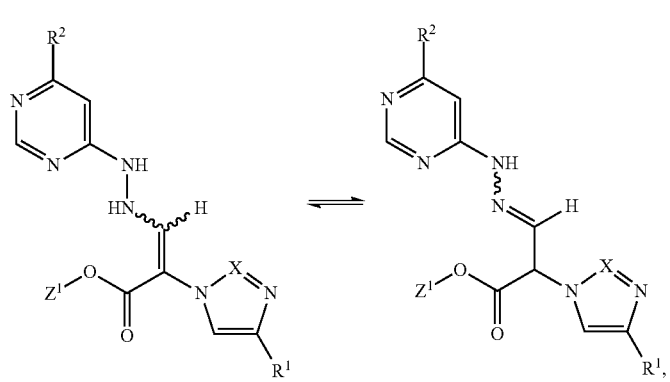

in which $Z^1$, $R^1$ and $R^2$ have the meaning given above,
which, already under these reaction conditions or in a subsequent reaction step under the influence of a base, cyclize to give the compounds of the formula (I), and the compounds of the formula (I) are, if appropriate with the appropriate (i) solvents and/or (ii) bases or acids, converted into their salts, their solvates, or the solvates of their salts, or

[B] compounds of the formula

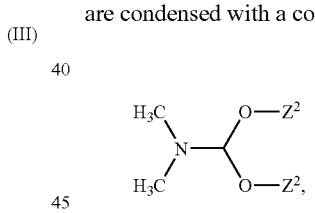

in which $Z^1$ and $R^1$ have the meaning given above,
are condensed with a compound of the formula (VI)

H₃C\
    N—CH(O—Z²)(O—Z²),
H₃C/ in which
$Z^2$ represents methyl or ethyl, to give compounds of the formula

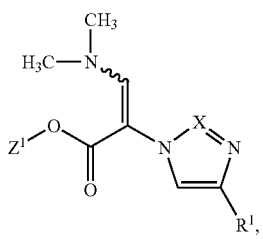

(VII)

in which $Z^1$ and $R^1$ have the meaning given above,
and then reacted in the presence of an acid with a compound of the formula (III) to give compounds of the formula (IV), which, already under these reaction conditions or in a subsequent reaction step under the influence of a base, cyclize to give the compounds of the formula (I),
and the compounds of the formula (I) are, if appropriate with the appropriate (i) solvents and/or (ii) bases or acids, converted into their salts, their solvates, or the solvates of their salts,
or
[C] the compound of the formula

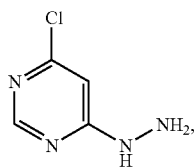

(VIII)

is, in water as the solvent in a one-pot process, reacted initially with compounds of the formula $$R^2\text{—H} \qquad (IX),$$

in which $R^2$ has the meaning given above,
and then with compounds of the formula (VII) to give compounds of the formula (I),
and the compounds of the formula (I) are, if appropriate with the appropriate (i) solvents and/or (ii) bases or acids, converted into their salts, their solvates, or the solvates of their salts.

The free base of the salts can be obtained by reacting the salts of the compounds or solvates of the salts of the compounds with a base.

Suitable bases are alkali metal hydroxides such as, for example, sodium hydroxide or potassium hydroxide, alkali metal or alkaline earth metal carbonates, such as sodium carbonate, potassium carbonate, calcium carbonate or caesium carbonate, or aqueous ammonia solution.

In an alternative process, the free base of the salts can be obtained, for example, by chromatography on a reversed-phase column using an acetonitrile/water gradient with addition of a base, in particular by using an RP18 Phenomenex Luna C18(2) column and the base diethylamine.

The invention furthermore provides a process for preparing the compounds of the formula (I) or solvates thereof where salts of the compounds or solvates of the salts of the compounds are converted by reaction with a base or by chromatography with addition of a base into the compounds.

Further compounds according to the invention can optionally also be prepared by conversions of functional groups of individual substituents, in particular those listed under $R^1$ and $R^2$, starting from the compounds of the formula (I) obtained by the above processes. These conversions are carried out by conventional methods known to the person skilled in the art and include, for example, reactions such as nucleophilic or electrophilic substitution, oxidation, reduction, hydrogenation, transition metal-catalysed coupling reactions, alkylation, acylation, amination, esterification, ester cleavage, etherification, ether cleavage, formation of carboxamides, sulphonamides, carbamates and ureas, and the introduction and removal of temporary protective groups.

Suitable inert solvents for the process steps (II)+(III)→(IV), (VII)+(III)→(IV) and (IV)→(I) are in particular ethers, such as diethyl ether, methyl tert-butyl ether, 1,2-dimethoxyethane, tetra-hydrofuran and dioxane, or alcohols, such as methanol, ethanol, n-propanol, isopropanol, n-butanol and tert-butanol, or water or mixtures of the solvents or a mixture of a solvent with water. Preference is given to using methanol, ethanol, tetrahydrofuran or water.

The process step (V)+(VI)→(VII) is preferably carried out in the solvent dimethylformamide or else in the presence of an excess of (VI) without further solvent. If appropriate, the reaction may also be carried out in an advantageous manner under microwave irradiation. The reaction is generally carried out in a temperature range of from +20° C. to +150° C., preferably at from +80° C. to +120° C. [cf. also J. P. Bazureau et al., *Synthesis* 1998, 967; ibid. 2001 (4), 581].

If appropriate, the process steps (II)+(III)→(IV) and (VII)+(III)→(IV) can be carried out in an advantageous manner with addition of an acid. Suitable for this purpose are customary inorganic or organic acids, such as, for example, hydrogen chloride, acetic acid, trifluoroacetic acid, methanesulphonic acid, p-toluenesulphonic acid or camphor-10-sulphonic acid. Preference is given to using acetic acid or in particular trifluoroacetic acid or p-toluenesulphonic acid.

The reaction (II)+(III)→(IV) is generally carried out in a temperature range of from 0° C. to +100° C., preferably from +10° C. to +50° C. The reaction (VII)+(III)→(IV) is generally carried out in a temperature range of from +20° C. to +120° C., preferably from +50° C. to +100° C.

The process sequences (II)+(III)→(IV)→(I) and (VII)+(III)→(IV)→(I) can be carried out as a two-step reaction or else as a one-pot reaction, without isolation of the intermediate (IV). Especially suitable for the latter variant is the reaction of the components under microwave irradiation; here, the reaction is generally carried out in a temperature range of from +50° C. to +200° C., preferably from +100° C. to +180° C.

There may be partial ring closure to (I) even during the preparation of (IV); in this case, the cyclization can, if required, be brought to completion by treating the reaction mixture in situ with a base.

Suitable bases for such a separate cyclization step (IV)→(I) are customary inorganic or organic bases. These include in particular alkali metal hydroxides, such as, for example, sodium hydroxide or potassium hydroxide, alkali metal carbonates or alkaline earth metal carbonates, such as sodium carbonate, potassium carbonate, calcium carbonate or caesium carbonate, alkali metal alkoxides, such as sodium methoxide or potassium methoxide, sodium ethoxide or potassium ethoxide or sodium tert-butoxide or potassium tert-butoxide, or alkali metal hydrides, such as sodium hydride. Preference is given to using sodium methoxide or sodium ethoxide.

The base-induced reaction (IV)→(I) is generally carried out in a temperature range of from 0° C. to +60° C., preferably at from 0° C. to +30° C.

The reaction (VIII)+(IX)+(VII)→(I) is generally carried out using from 1.1 to 2.0 equivalents of (IX) per equivalent of (VIII), if appropriate in the presence of from 1.1 to 2.0 equivalents of a base. Preferred is the reaction with from 1.1 to 1.5 equivalents of (IX).

Suitable bases for the reaction (VIII)+(IX)+(VII)→(I) are customary inorganic or organic bases. These include in particular alkali metal hydroxides, such as, for example, sodium hydroxide or potassium hydroxide, or amine bases, such as, for example, N-ethyl-N-(propan-2-yl)propane-2-amine.

The compounds of the formula (II) can be prepared from compounds of the formula (V) by methods customarily used in the literature for the C-acylation of carboxylic esters. The compounds of the formulae (III), (V), (VI), (VIII) and (IX) are commercially available, known from the literature or can be prepared analogously to processes described in the literature.

The preparation of the compounds according to the invention can be illustrated by Reaction Scheme 2 below:

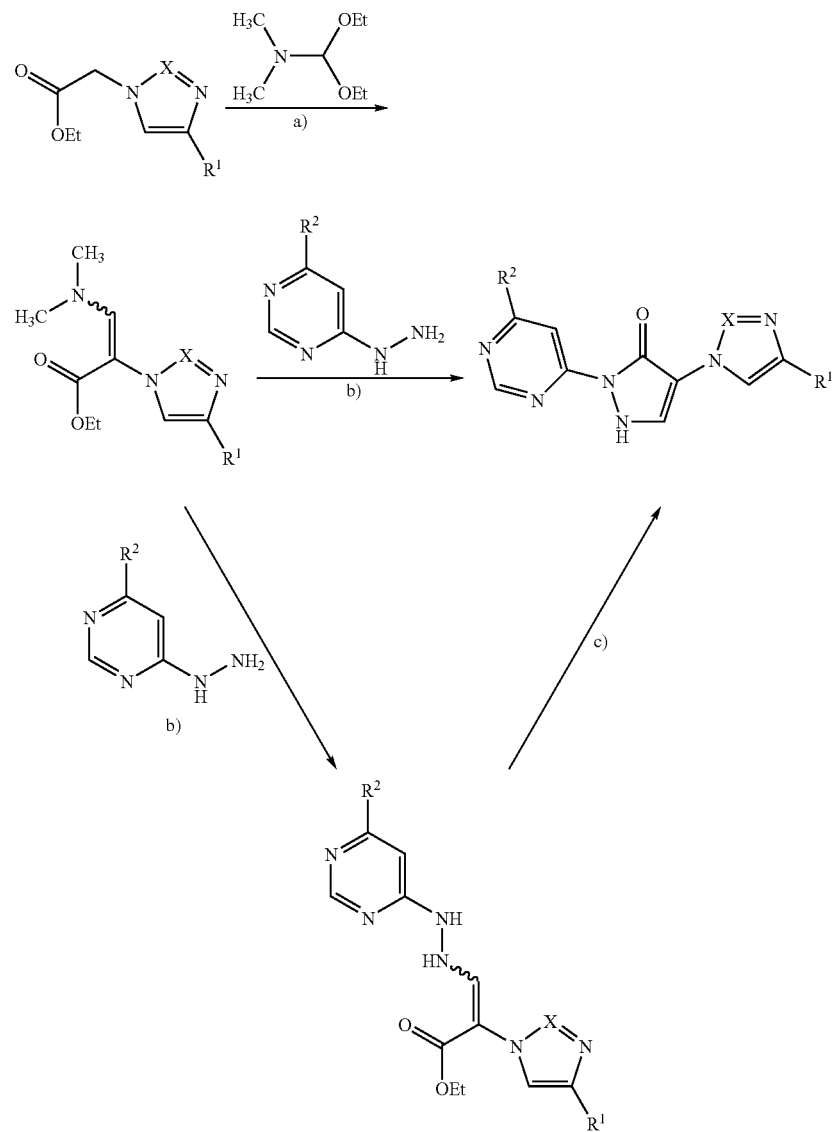

Preference is given to N-ethyl-N-(propan-2-yl)propane-2-amine.

The reaction (VIII)+(IX)+(VII)→(I) is generally carried out in a temperature range of from +20° C. to +100° C., preferably at from +70° C. to +100° C.

All process steps can be carried out at atmospheric, elevated or reduced pressure (for example from 0.5 to 5 bar). In general, the reactions are carried out at atmospheric pressure.

[a]: DMF, 16 h, +100° C.; b): ethanol, trifluoroacetic acid, +78° C.; c): NaOEt, ethanol, 1 h, RT].

The compounds according to the invention show an unforeseeable, valuable pharmacological action spectrum.

They are therefore suitable for use as medicaments for treatment and/or prophylaxis of diseases in humans and animals.

The compounds according to the invention are distinguished as specific inhibitors of HIF prolyl 4-hydroxylases.

On the basis of their pharmacological properties, the compounds according to the invention can be employed for treatment and/or prophylaxis of cardiovascular diseases, in particular cardiac insufficiency, coronary heart disease, angina pectoris, myocardial infarction, stroke, arteriosclerosis, essential, pulmonary and malignant hypertension and peripheral arterial occlusive disease.

The compounds according to the invention are furthermore suitable for treatment and/or prophylaxis of blood formation disorders, such as e.g. idiopathic anaemias, renal anaemia and anaemias accompanying a tumour disease (in particular an anaemia induced by chemotherapy), an infection (in particular HIV infection) or another inflammatory disease, such as e.g. rheumatoid arthritis. The compounds according to the invention are moreover suitable for supporting treatment of anaemias as a result of blood loss, iron deficiency anaemia, vitamin deficiency anaemia (e.g. as a result of vitamin B12 deficiency or as a result of folic acid deficiency), hypoplastic and aplastic anaemia or haemolytic anaemia, or for supporting treatment of anaemias as a result of iron utilization disorders (sideroachrestic anaemia) or anaemias as a result of other endocrine disorders (e.g. hypothyroidosis).

The compounds are furthermore suitable for increasing the haematocrit with the aim of obtaining blood for autodonation of blood before operations.

The compounds according to the invention can moreover be used for treatment and/or prophylaxis of operation-related states of ischaemia and consecutive symptoms thereof after surgical interventions, in particular interventions on the heart using a heart-lung machine (e.g. bypass operations, heart valve implants), interventions on the carotid arteries, interventions on the aorta and interventions with instrumental opening or penetration of the skull cap. The compounds are furthermore suitable for general treatment and/or prophylaxis in the event of surgical interventions with the aim of accelerating wound healing and shortening the convalescence time.

The compounds are moreover suitable for treatment and prophylaxis of consecutive symptoms of acute and protracted ischaemic states of the brain (e.g. stroke, birth asphyxia).

The compounds can furthermore be employed for treatment and/or prophylaxis of cancer and for treatment and/or prophylaxis of an impairment in the state of health occurring in the course of treatment of cancer, in particular after therapy with cytostatics, antibiotics and irradiations.

The compounds are furthermore suitable for treatment and/or prophylaxis of diseases of the rheumatic type and other disease forms to be counted as autoimmune diseases, and in particular for treatment and/or prophylaxis of an impairment in the state of health occurring in the course of medicamentous treatment of such diseases.

The compounds according to the invention can moreover be employed for treatment and/or prophylaxis of diseases of the eye (e.g. glaucoma), the brain (e.g. Parkinson's disease, Alzheimer's disease, dementia, chronic pain sensation), of chronic kidney diseases, renal insufficiency and acute renal failure and for promoting wound healing.

The compounds are moreover suitable for treatment and/or prophylaxis of general physical weakness, up to cachexia, in particular occurring to an increased extent at a more elderly age.

The compounds are furthermore suitable for treatment and/or prophylaxis of sexual dysfunction.

The compounds are moreover suitable for treatment and/or prophylaxis of diabetes mellitus and its consecutive symptoms, such as e.g. diabetic macro- and microangiopathy, diabetic nephropathy and neuropathy.

The compounds according to the invention are moreover suitable for treatment and/or prophylaxis of fibrotic diseases e.g. of the heart, the lungs and the liver.

In particular, the compounds according to the invention are also suitable for prophylaxis and treatment of retinopathy in premature babies (retinopathia prematurorum).

The present invention moreover provides the use of the compounds according to the invention for treatment and/or prevention of diseases, in particular the abovementioned diseases.

The present invention moreover provides the use of the compounds according to the invention for the preparation of a medicament for treatment and/or prevention of diseases, in particular the abovementioned diseases.

The present invention moreover provides a method for treatment and/or prevention of diseases, in particular the abovementioned diseases, using an active amount of at least one of the compounds according to the invention.

The compounds according to the invention can be employed by themselves or, if required, in combination with other active compounds. The present invention moreover provides medicaments comprising at least one of the compounds according to the invention and one or more further active compounds, in particular for treatment and/or prevention of the abovementioned diseases. Suitable active compounds in the combination which may be mentioned by way of example and preferably are: ACE inhibitors, angiotensin II receptor antagonists, beta receptor blockers, calcium antagonists, PDE inhibitors, mineralocorticoid receptor antagonists, diuretics, aspirin, iron supplements, vitamin B12 and folic acid supplements, statins, digitalis (digoxin) derivatives, tumour chemotherapeutics and antibiotics.

In a preferred embodiment of the invention, the compounds according to the invention are administered in combination with an ACE inhibitor, such as, by way of example and preferably, enalapril, captopril, lisinopril, ramipril, delapril, fosinopril, quinopril, perindopril or trandopril.

In a preferred embodiment of the invention, the compounds according to the invention are administered in combination with an angiotensin AII antagonist, such as, by way of example and preferably, losartan, candesartan, valsartan, telmisartan or embusartan.

In a preferred embodiment of the invention, the compounds according to the invention are administered in combination with a beta receptor blocker, such as, by way of example and preferably, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with a calcium antagonist, such as, by way of example and preferably, nifedipine, amlopidine, verapamil or diltiazem.

In a preferred embodiment of the invention, the compounds according to the invention are administered in combination with a phosphodiesterase (PDE) inhibitor, such as, by way of example and preferably, milrinone, aminone, pimobendan, cilostazol, sildenafil, vardenafil or tadalafil.

In a preferred embodiment of the invention, the compounds according to the invention are administered in combination with a mineralocorticoid receptor antagonist, such as, by way of example and preferably, spironolactone, eplerenone, canrenone or potassium canrenoate.

In a preferred embodiment of the invention the compounds according to the invention are administered in combination with a diuretic, such as, by way of example and preferably, furosemide, bumetamide, torsemide, bendroflumethiazide, chlorothiazide, hydrochlorothiazide, hydroflumethiazide, methylclothiazide, polythiazide, trichloromethiazide, chlorthalidone, indapamide, metolazone, quinethazone, acetazolamide, dichlorphenamide, methazolamide, glycerine, isosorbide, mannitol, amiloride or triamteren.

In a preferred embodiment of the invention, the compounds according to the invention are administered in combination with an HMG-CoA reductase inhibitor from the class of statins, such as, by way of example and preferably, lovastatin, simvastatin, pravastatin, fluvastatin, atorvastatin, rosuvastatin, cerivastatin or pitavastatin.

In a preferred embodiment of the invention, the compounds according to the invention are administered in combination with a tumour chemotherapeutic, by way of example and preferably from the group consisting of platinum complexes, such as e.g. cisplatin and carboplatin, the alkylating agents, such as e.g. cyclophosphamide and chlorambucil, the antimetabolites, such as e.g. 5-fluorouracil and methotrexate, the topoisomerase inhibitors, such as e.g. etoposide and camptothecin, the antibiotics, such as e.g. doxorubicin and daunorubicin, or the kinase inhibitors, such as e.g. sorafenib and sunitinib.

In a preferred embodiment of the invention, the compounds according to the invention are administered in combination with an antibiotic, by way of example and preferably from the group consisting of penicillins, cephalosporins or quinolones, such as e.g. ciprofloxacin and moxifloxacin.

The present invention moreover provides medicaments which comprise at least one compound according to the invention, conventionally together with one or more inert, non-toxic, pharmaceutically suitable auxiliary substances, and the use thereof for the above-mentioned purposes.

The compounds according to the invention can act systemically and/or locally. They can be administered in a suitable manner for this purpose, such as e.g. orally, parenterally, pulmonally, nasally, sublingually, lingually, buccally, rectally, dermally, transdermally, conjunctivally, optically or as an implant or stent.

The compounds according to the invention can be administered in suitable administration forms for these administration routes.

Administration forms which function according to the prior art, release the compounds according to the invention rapidly and/or in a modified manner and comprise the compounds according to the invention in crystalline and/or amorphized and/or dissolved form are suitable for oral administration, such as e.g. tablets (non-coated or coated tablets, for example coatings which are resistant to gastric juice or dissolve in a delayed manner or are insoluble and control the release of the compound according to the invention), tablets or films/oblates, films/lyophilizates or capsules which disintegrate rapidly in the oral cavity (for example hard or soft gelatin capsules), sugar-coated tablets, granules, pellets, powders, emulsions, suspensions, aerosols or solutions.

Parenteral administration can be effected with bypassing of an absorption step (e.g. intravenously, intraarterially, intracardially, intraspinally or intralumbarly) or with inclusion of an absorption (e.g. intramuscularly, subcutaneously, intracutaneously, percutaneously or intraperitoneally). Administration forms which are suitable for parenteral administration are, inter alia, injection and infusion formulations in the form of solutions, suspensions, emulsions, lyophilizates or sterile powders.

For the other administration routes e.g. inhalation medicament forms (inter alia powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents are suitable.

Oral and parenteral administration are preferred, in particular oral and intravenous administration.

The compounds according to the invention can be converted into the administration forms mentioned. This can be effected in a manner known per se by mixing with inert, non-toxic, pharmaceutically suitable auxiliary substances. These auxiliary substances include inter alia carrier substances (for example microcrystalline cellulose, lactose, mannitol), solvents (e.g. liquid polyethylene glycols), emulsifiers and dispersing or wetting agents (for example sodium dodecyl sulphate, polyoxysorbitan oleate), binders (for example polyvinylpyrrolidone), synthetic and natural polymers (for example albumin), stabilizers (e.g. antioxidants, such as, for example, ascorbic acid), dyestuffs (e.g. inorganic pigments, such as, for example, iron oxides) and flavour and/or smell correctants.

In general, it has proved advantageous in the case of parenteral administration to administer amounts of from about 0.001 to 1 mg/kg, preferably about 0.01 to 0.5 mg/kg of body weight to achieve effective results. In the case of oral administration the dosage is about 0.01 to 100 mg/kg, preferably about 0.01 to 20 mg/kg and very particularly preferably 0.1 to 10 mg/kg of body weight.

Nevertheless it may be necessary to deviate from the amounts mentioned, and in particular depending on the body weight, administration route, individual behaviour towards the active compound, nature of the formulation and point of time or interval at which administration takes place. Thus in some cases it may be sufficient to manage with less than the above-mentioned minimum amount, while in other cases the upper limit mentioned must be exceeded. In the case where relatively large amounts are administered, it may be advisable to distribute these into several individual doses over the day.

The following embodiment examples illustrate the invention. The invention is not limited to the examples.

The percentage data in the following tests and examples are percentages by weight, unless stated otherwise; parts are parts by weight. The solvent ratios, dilution ratios and concentration data of liquid/liquid solutions in each case relate to the volume.

EXAMPLES

| Abbreviations: | |
|---|---|
| aq. | aqueous solution |
| cat. | catalytic |
| d | day(s) |
| DCI | direct chemical ionization (in MS) |
| DMF | dimethylformamide |
| DMSO | dimethyl sulphoxide |
| EI | electron impact ionization (in MS) |
| ESI | electrospray ionization (in MS) |
| Et | ethyl |
| GC-MS | gas chromatography-coupled mass spectroscopy |
| h | hour(s) |
| HPLC | high pressure, high performance liquid chromatography |
| conc. | concentrated |
| LC-MS | liquid chromatography-coupled mass spectroscopy |

| Abbreviations: | |
|---|---|
| Meth. | method |
| min | minute(s) |
| MS | mass spectroscopy |
| NMR | nuclear magnetic resonance spectroscopy |
| R$_t$ | retention time (in HPLC) |
| RT | room temperature |
| TFA | trifluoroacetic acid |
| THF | tetrahydrofuran |

LC-MS, GC-MS and HPLC Methods:

Method 1 (LC-MS): instrument: Micromass Platform LCZ with HPLC Agilent series 1100; column: Thermo Hypersil GOLD 3μ, 20 mm×4 mm; mobile phase A: 1 l of water+0.5 ml of 50% strength formic acid, mobile phase B: 1 l acetonitrile+0.5 ml of 50% strength formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 2 (LC-MS): instrument type MS: Micromass ZQ; instrument type HPLC: Waters Alliance 2795; column: Phenomenex Synergi 2μ Hydro-RP Mercury 20 mm×4 mm; mobile phase A: 1 l of water+0.5 ml of 50% strength formic acid, mobile phase B: 1 l acetonitrile+0.5 ml of 50% strength formic acid; gradient: 0.0 min 90% A→2.5 min 30% A→3.0 min 5% A→4.5 min 5% A; flow rate: 0.0 min 1 ml/min ~2.5 min/3.0 min/4.5 min 2 ml/min; oven: 50° C.; UV detection: 210 nm.

Method 3 (LC-MS): instrument type MS: Micromass ZQ; instrument type HPLC: Waters Alliance 2795; column: Phenomenex Synergi 2.5μ MAX-RP 100A Mercury 20 mm×4 mm; mobile phase A: 1 l of water+0.5 ml of 50% strength formic acid, mobile phase B: 1 l acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 4 (LC-MS): instrument: Micromass Quattro Micro MS with HPLC Agilent series 1100; column: Thermo Hypersil GOLD 3μ 20 mm×4 mm; mobile phase A: 1 l of water+0.5 ml of 50% strength formic acid, mobile phase B: 1 l acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 5 (LC-MS): instrument: Micromass QuattroPremier with Waters HPLC Acquity; column: Thermo Hypersil GOLD 1.9μ 50 mm×1 mm; mobile phase A: 1 l of water+0.5 ml of 50% strength formic acid, mobile phase B: 1 l acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

Method 6 (HPLC): instrument: HP 1100 with DAD detection; column: Kromasil 100 RP-18, 60 mm×2.1 mm, 3.5 μm; mobile phase A: 5 ml of perchloric acid (70% strength)/litre of water, mobile phase B: acetonitrile; gradient: 0 min 2% B→0.5 min 2% B→4.5 min 90% B→6.5 min 90% B→6.7 min 2% B→7.5 min 2% B; flow rate: 0.75 ml/min; column temperature: 30° C.; UV detection: 210 nm.

Method 7 (GC-MS): instrument: Micromass GCT, GC6890; column: Restek RTX-35, 15 m×200 μm×0.33 μm; constant helium flow: 0.88 ml/min; oven: 70° C.; inlet: 250° C.; gradient: 70° C., 30° C./min ~310° C. (maintained for 3 min).

Method 8 (preparative HPLC): column: Kromasil 100 C18 5 μm, 250 mm×20 mm; mobile phase A: Milli-Q water, mobile phase B: aqueous 0.1% strength trifluoroacetic acid, mobile phase C: acetonitrile; gradient: 0.0 min 76% A, 5% B, 19% C→15 min 4% A, 95% B, 1% C→15.1 min 76% A, 5% B, 19% C→20 min 76% A, 5% B, 19% C; oven: 40° C.; flow rate: 25 ml/min; UV detection: 210 nm.

Method 9 (preparative HPLC): column: Sunfire C18 5 μm, 19 mm×150 mm; mobile phase A: aqueous 0.2% strength trifluoroacetic acid, mobile phase B: acetonitrile; gradient: 0.0 min 95% A 8 min 50% A→8.01 min 95% A→12 min 95% A; RT; flow rate: 25 ml/min; UV detection: 210 nm.

Method 10 (preparative HPLC): column: Sunfire C18 5 μm, 19 mm×150 mm; mobile phase A: aqueous 0.2% strength trifluoroacetic acid, mobile phase B: acetonitrile; 0 min 90% A→13 min 90% A; oven: 40° C.; flow rate: 25 ml/min; UV detection: 210 nm.

Method 11 (preparative HPLC): column: XBridge C18 5 μm, 19 mm×150 mm; mobile phase A: aqueous 0.2% strength formic acid, mobile phase B: acetonitrile; 0 min 75% A→6 min 75% A; RT; flow rate: 25 ml/min; UV detection: 210 nm.

Method 12 (preparative HPLC): column: XBridge C18 5 μm, 19 mm×150 mm; mobile phase A: aqueous 0.2% strength formic acid, mobile phase B: acetonitrile; 0 min 93% A→4 min 93% A; RT; flow rate: 25 ml/min; UV detection: 210 nm.

Method 13 (preparative HPLC): column: XBridge C18 5 μm, 19 mm×150 mm; mobile phase A: aqueous 0.2% strength trifluoroacetic acid, mobile phase B: acetonitrile; 0 min 90% A→12 min 90% A; oven: 40° C.; flow rate: 25 ml/min; UV detection: 210 nm.

Starting Materials

Example 1A

Ethyl (4-cyano-1H-imidazol-1-yl)acetate

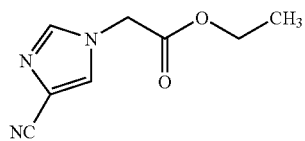

3.3 g (35.3 mmol) of 1H-imidazole-4-carbonitrile [Matthews et al., *J. Org. Chem.* 1986, 51, 3228-3231] are initially charged in 13.2 ml (11.5 g, 35.3 mmol) of 21% strength sodium ethoxide solution in ethanol, and 4.3 ml (6.5 g, 38.9 mmol) of ethyl bromoacetate are added. The reaction mixture is stirred at RT for 16 h. For work-up, the precipitated solid is filtered off, the filter residue is washed with ethanol and the filtrate is concentrated under reduced pressure. Diisopropyl ether is added to the residue, the mixture is filtered again, the filtrate is once more concentrated on a rotary evaporator and the residue is dried under reduced pressure. Yield: 3.8 g (60% of theory)

LC-MS (Method 1): R$_t$=1.17 min; MS (ESIpos): m/z=180 [M+H]$^+$;

$^1$H-NMR (400 MHz, DMSO-d$_6$): δ=8.12 (s, 1H), 7.88 (s, 1H), 5.06 (s, 2H), 4.18 (q, 2H), 1.22 (t, 3H).

Example 2A

Ethyl 2-(1H-1,2,3-triazol-1-yl)acetate

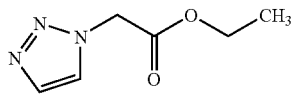

129.2 g (5.6 mmol) of sodium are added slowly to 4.0 litres of ethanol. 400.0 g (5.6 mol) of 1,2,3-1H-triazole are then added, and 623 ml (938.2 g, 5.6 mol) of ethyl bromoacetate are added dropwise at an internal temperature of 20-25° C. The mixture is stirred at RT for 48 h. The precipitated solid is filtered off, the ethanol is removed under reduced pressure and the mixture is filtered again. The residue is taken up in ethyl acetate, filtered, again concentrated under reduced pressure and purified by distillation on a 30 cm column. The product is obtained at a bath temperature of 140° C., a head temperature of 60-115° C. and a pressure of 1 mbar. Yield: 440.0 g (50% of theory)

HPLC (Method 6): $R_t$=1.58 min;

LC-MS (Method 1): $R_t$=0.71 min; MS (ESIpos): m/z=156 [M+H]$^+$.

Example 3A

Ethyl 1H-imidazol-1-ylacetate

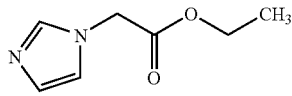

118.2 g (5.1 mmol) of sodium are added slowly to 2.5 litres of ethanol. 350.0 g (5.1 mol) of imidazole and 570 ml (858.6 g, 5.1 mol) of ethyl bromoacetate are added dropwise at an internal temperature of 20-25° C. The mixture is stirred at RT for 24 h. The precipitated solid is filtered off, the ethanol is removed under reduced pressure and the mixture is filtered again. The residue is purified by column chromatography on silica gel (mobile phase ethyl acetate). Yield: 639.0 g (81% of theory)

GC-MS (Method 7): $R_t$=4.55 min; MS (ESIpos): m/z=155 [M+H]$^+$.

Example 4A

Ethyl (4-cyano-1H-1,2,3-triazol-1-yl)acetate

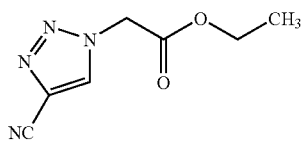

4.1 g (31.9 mmol) of ethyl azidoacetate and 2.8 g (31.9 mmol) of 2-chloroacrylonitrile are stirred in 32 ml of water at a bath temperature of 80° C. for 16 h. After cooling to RT, the solution is acidified with 1 N hydrochloric acid and extracted with ethyl acetate. The organic phase is dried over sodium sulphate, filtered and concentrated under reduced pressure. 50 ml of ethanol and 10 drops of concentrated sulphuric acid are added to the residue, and the mixture is stirred under reflux for 16 h. For work-up, the reaction mixture is concentrated under reduced pressure, ethyl acetate is added to the residue, the suspension is washed with semiconcentrated sodium bicarbonate solution and the organic phase is dried over sodium sulphate. The solvent is removed completely on a rotary evaporator and the solid is dried under reduced pressure. Yield: 1.5 g (25% of theory)

LC-MS (Method 3): $R_t$=0.96 min; MS (ESIpos): m/z=181 [M+H]$^+$;

$^1$H-NMR (400 MHz, DMSO-d$_6$): δ=9.06 (s, 1H), 5.57 (s, 2H), 4.19 (q, 2H), 1.22 (t, 3H).

Example 5A

Ethyl 3-(N,N-dimethylamino)-2-(1H-imidazol-1-yl)acrylate

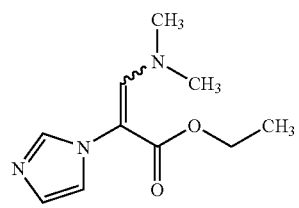

38.0 g (244.9 mmol) of the compound from Example 3A are stirred in 126 ml (108.1 g, 734.7 mmol) of N,N-dimethylformamide diethyl acetal at a bath temperature of 90° C. for 16 h. After cooling, the mixture is concentrated under reduced pressure, the residue is stirred with diisopropyl ether and the solid is filtered off and finally washed with diisopropyl ether. Yield: 49.0 g (95% of theory)

LC-MS (Method 2): $R_t$=2.42 min; MS (ESIpos): m/z=211 [M+H]$^+$;

$^1$H-NMR (400 MHz, DMSO-d$_6$): δ=7.52 (s, 1H), 7.49 (s, 1H), 7.05 (s, 1H), 6.91 (s, 1H), 4.02 (q, 2H), 2.63 (br. s, 6H), 1.12 (t, 3H).

Example 6A

Ethyl 3-(N,N-dimethylamino)-2-(4-cyano-1H-imidazol-1-yl)acrylate

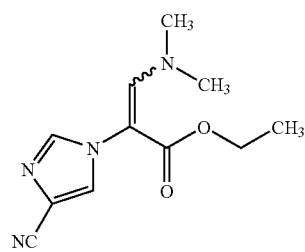

3.8 g (21.4 mmol) of the compound from Example 1A and 7.4 ml (6.3 g, 42.8 mmol) of N,N-dimethylformamide diethyl acetal are stirred at a bath temperature of 100° C. for 16 h. For work-up, the cooled reaction solution is concentrated on a rotary evaporator and the residue is dried under reduced pressure. Yield: 5.0 g (73% pure, 73% of theory)

LC-MS (Method 1): $R_t$=2.69 min; MS (ESIpos): m/z=235 [M+H]$^+$;

$^1$H-NMR (400 MHz, DMSO-d$_6$): δ=8.13 (s, 1H), 7.85 (s, 1H), 7.58 (s, 1H), 4.03 (q, 2H), 2.69 (br. s, 6H), 1.12 (t, 3H).

Example 7A

Ethyl 3-(dimethylamino)-2-(4-cyano-1H-1,2,3-triazol-1-yl)acrylate

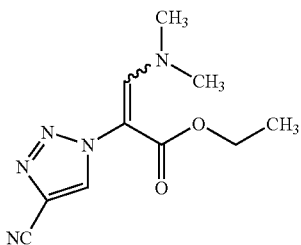

1.3 g (7.5 mmol) of the compound from Example 4A and 1.4 ml (1.2 g, 8.2 mmol) of N,N-dimethylformamide diethyl acetal are stirred at a bath temperature of 100° C. for 16 h. For work-up, the cooled reaction solution is concentrated on a rotary evaporator and the residue is dried under reduced pressure. Yield: 1.5 g (86% of theory)

LC-MS (Method 4): $R_t$=1.55 min; MS (ESIpos): m/z=236 [M+H]$^+$;

$^1$H-NMR (400 MHz, DMSO-d$_6$): δ=9.14 (s, 1H), 7.75 (s, 1H), 4.04 (q, 2H), 3.15 (br. s, 3H), 2.18 (br. s, 3H), 1.13 (t, 3h).

Example 8A

Ethyl 3-(dimethylamino)-2-(1H-1,2,3-triazol-1-yl)acrylate

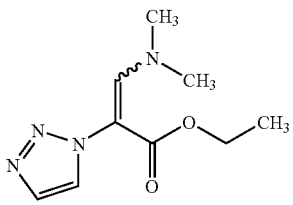

44.2 ml (38.0 g, 257.8 mmol) of N,N-dimethylformamide diethyl acetal are added to 20.0 g (128.9 mmol) of the compound from Example 2A, and the mixture is stirred at 100° C. for 16 h. After cooling to RT, the reaction mixture is concentrated under reduced pressure. The residue is triturated with diethyl ether, filtered off and washed with diethyl ether. Yield: 18.0 g (67% of theory)

LC-MS (Method 4): $R_t$=1.20 min; MS (ESIpos): m/z=211 [M+H]$^+$.

$^1$H-NMR (400 MHz, DMSO-d$_6$): δ=8.10 (d, 1H), 7.78 (d, 1H), 7.65 (s, 1H), 4.03 (q, 2H), 3.06 (br. s, 3H), 2.10 (br. s, 3H), 1.12 (t, 3H).

Example 9A 4-(4-Cyclobutylpiperazin-1-yl)-6-hydrazinopyrimidine

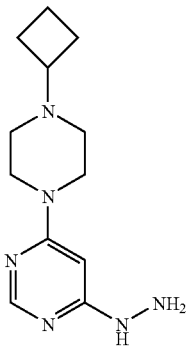

Step a):
4-Chloro-6-(4-cyclobutylpiperazin-1-yl)pyrimidine

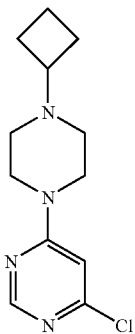

1.8 g (8.4 mmol) of 1-cyclobutylpiperazine dihydrochloride (Zaragoza et al., *J. Med. Chem.* 2004, 47, 2833) are initially charged in 18 ml of water, and 2.9 ml (2.1 g, 16.9 mmol) of N-ethyl-N-(propan-2-yl)propane-2-amine are added. The mixture is stirred at RT for 30 min, and 1.3 g (8.4 mmol) of 4,6-dichloropyrimidine are added. The reaction mixture is stirred at 115° C. for 1 h and cooled to RT, 25 ml of ethyl acetate are added and the mixture is extracted with 25 ml of a saturated aqueous sodium bicarbonate solution. The organic phase is separated off, dried over sodium sulphate, filtered and concentrated under reduced pressure. The crude product is purified by column chromatography on silica gel (mobile phase: dichloromethane/methanol 100/3). Yield: 1.9 g (89% of theory)

HPLC (Method 6): $R_t$=2.79 min; MS (DCI): m/z=254 [M+H]$^+$;

¹H-NMR (400 MHz, DMSO-d₆): δ=8.32 (s, 1H), 6.95 (s, 1H), 3.65-3.58 (m, 4H), 2.70 (quintet, 1H), 2.27 (t, 4H), 2.00-1.93 (m, 2H), 1.87-1.75 (m, 2H), 1.67-1.55 (m, 2H).

Step b): 4-(4-Cyclobutylpiperazin-1-yl)-6-hydrazinopyrimidine

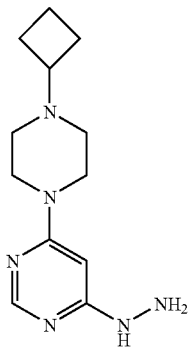

At RT, 4.4 ml (4.5 g, 89.7 mmol) of hydrazine hydrate are added dropwise with stirring to a solution of 1.9 g (7.5 mmol) of 4-chloro-6-(4-cyclobutylpiperazin-1-yl)pyrimidine in 28 ml of ethanol. The reaction solution is stirred at 80° C. for 16 h. For work-up, the mixture is concentrated under reduced pressure, the residue is triturated repeatedly with diethyl ether, and the precipitated solid is filtered off and dried under reduced pressure. The residue is then purified by column chromatography on silica gel (mobile phase dichloromethane/methanol 10/2). Yield: 1.5 g (80% of theory)

LC-MS (Method 6): $R_t$=1.36 min; MS (ESIpos): m/z=249 [M+H]⁺;

¹H-NMR (400 MHz, DMSO-d₆): δ=7.92 (s, 1H), 7.63 (s, 1H), 5.90 (NH), 4.09 (s, NH2), 3.45 (t, 4H), 2.69 (quintet, 1H), 2.26 (t, 4H), 2.00-1.93 (m, 2H), 1.82-1.75 (m, 2H), 1.67-1.60 (m, 2H).

Example 10A 1-(6-Hydrazinylpyrimidin-4-yl)azetidin-3-ol

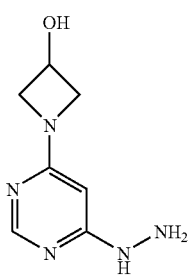

Step a): 1-(6-Chloropyrimidin-4-yl)azetidin-3-ol

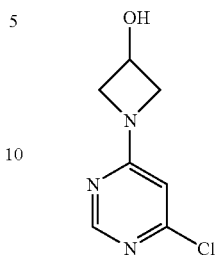

7.3 g (48.7 mmol) of 4,6-dichloropyrimidine are suspended in 140 ml of water, and 47 ml 1 N aqueous sodium hydroxide solution are added. 5.3 g (48.7 mmol) of 3-hydroxyazetidine are added, and the reaction mixture is stirred at 90° C. for 3 d. After cooling to RT, the reaction mixture is concentrated under reduced pressure and reacted further without further purification.

LC-MS (Method 5): $R_t$=0.36 min; MS (ESIpos): m/z=1.87 [M+H]⁺.

Step b): 1-(6-Hydrazinylpyrimidin-4-yl)azetidin-3-ol

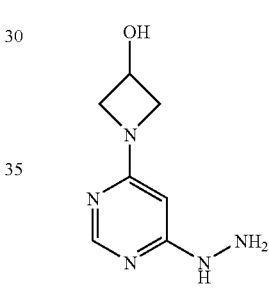

At RT, 27.2 ml (27.9 g, 279.1 mmol) of hydrazine hydrate are added dropwise with stirring to a solution of 10.4 g (55.8 mmol) of 1-(6-chloropyrimidin-4-yl)azetidin-3-ol in 100 ml of ethanol. The reaction solution is stirred at 80° C. for 16 h. For work-up, the mixture is concentrated under reduced pressure, and the precipitate is filtered off and washed twice with in each case 10 ml of ethanol. Yield: 2.0 g (19% of theory)

LC-MS (Method 1): $R_t$=2.06 min; MS (ESIpos): m/z=194 [M+H]⁺.

Example 11A

4-Chloro-6-hydrazinopyrimidine

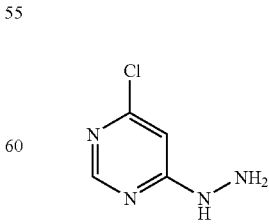

At RT, 11.8 ml (12.1 g, 241.6 mmol) of hydrazine hydrate are added dropwise with stirring to a solution of 20.0 g (134.3 mmol) of 4,6-dichloropyrimidine in 300 ml of ethanol. If the solution becomes turbid during the metered addition of the hydrazine hydrate, further ethanol (about 400 ml) is added. The reaction solution is stirred at RT for 12 h. For work-up, the precipitated solid is filtered off, the filter residue is washed twice with in each case 150 ml of water and twice with in each case 100 ml of diethyl ether and the product is dried under reduced pressure. The concentrated mother liquor gives a further crystalline product fraction. Yield: 16.8 g (87% of theory)

LC-MS (Method 1): $R_t$=1.17 min; MS (ESIpos): m/z=145 [M+H]$^+$;

$^1$H-NMR (400 MHz, DMSO-d$_6$): δ=8.81 (s, 1H), 8.17 (br. s, 1H), 6.75 (s, 1H), 4.48 (br. s, 2H).

Example 12A 2-(6-Chloropyrimidin-4-yl)-4-(1H-1,2,3-triazol-1-yl)-1,2-dihydro-3H-pyrazol-3-one hydrochloride

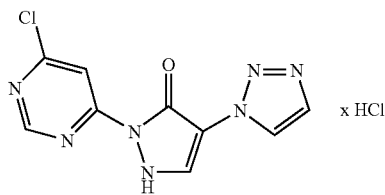

10.0 g (47.7 mmol) of the compound from Example 8A and 8.3 g (57.1 mmol) of the compound from Example 11A are initially charged in 100 ml of ethanol, and 1.5 ml (2.2 g, 19.0 mmol) of trifluoroacetic acid are added. The mixture is stirred under reflux for 12 h. An excess of a 4 M solution of hydrogen chloride in dioxane is then added to the cooled reaction mixture, the mixture is stirred for about 1 h, the precipitated crystals are filtered off and the filter residue is washed with dioxane and ethanol. The intermediate obtained in this manner is dissolved in 150 ml of ethanol, 50 ml of a 25% strength methanolic sodium methoxide solution are added and the mixture is stirred at RT for 2 h. The reaction mixture is then adjusted with 1 N hydrochloric acid to pH=5 and stirred at RT for a further 2 h, the solid is filtered off, the filter residue is washed with ethanol and the product is dried under reduced pressure. Yield: 7.0 g (49% of theory)

LC-MS (Method 5): $R_t$=1.20 min; MS (ESIpos): m/z=264 [M+H]$^+$.

Example 13A 2-(6-Chloropyrimidin-4-yl)-4-(1H-imidazol-1-yl)-1,2-dihydro-3H-pyrazol-3-one hydrochloride

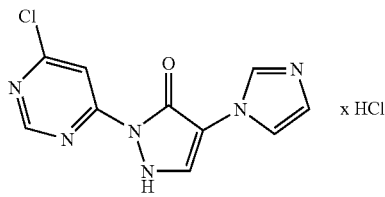

10.0 g (47.8 mmol) of the compound from Example 5A and 8.3 g (57.3 mmol) of the compound from Example 11A are initially charged in 100 ml of ethanol, and 1.5 ml (2.2 g, 19.0 mmol) of trifluoroacetic acid are added. The mixture is stirred under reflux for 12 h. The precipitated crystals are filtered off, the filter residue is washed with ethanol and the intermediate is dried under reduced pressure overnight. The intermediate is then suspended in 20 ml of methanol, 100 ml of a 4 M solution of hydrogen chloride in dioxane are added and the mixture is stirred at RT for 1 h. The solid is filtered off, the filter residue is washed with dioxane, ethyl acetate and diisopropyl ether and the product is dried under reduced pressure. Yield: 4.6 g (32% of theory)

HPLC (Method 6): $R_t$=2.81 min; MS (ESIpos): m/z=263 [M+H]$^+$;

$^1$H-NMR (400 MHz, DMSO-d$_6$): δ=9.46 (s, 1H), 8.96 (s, 1H), 8.56 (s, 1H), 8.51 (d, 1H), 8.07-8.04 (m, 1H), 7.85-7.82 (m, 1H).

Example 14A 4-(6-Hydrazinylpyrimidin-4-yl)-1,4-oazepane

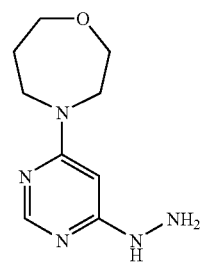

Step a): 4-(6-Chloropyrimidin-4-yl)-1,4-oxazepane

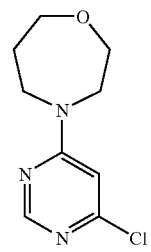

A mixture of 3.0 g (20.1 mmol) of 4,6-dichloropyrimidine, 2.8 g (20.1 mmol) of 1,4-oxazepane hydrochloride and 6.4 g (60.4 mmol) of sodium carbonate in 45 ml of water is stirred under reflux for 16 h. After cooling to RT, the reaction mixture is extracted with ethyl acetate. The organic phase is washed with saturated sodium chloride solution, dried over sodium sulphate and filtered. Under reduced pressure, the filtrate is concentrated to dryness. The product is obtained as an oil. Yield: 3.9 g (86% of theory)

LC-MS (Method 4): $R_t$=1.32 min; MS (ESIpos): m/z=214 [M+H]$^+$;

$^1$H-NMR (400 MHz, DMSO-d$_6$): δ=8.33 (s, 1H), 6.86 (s, 1H), 3.99-3.52 (m, 8H), 1.84 (m, 2H).

Step b):
4-(6-Hydrainylpyrimidin-4-yl)-1,4-oxazepane

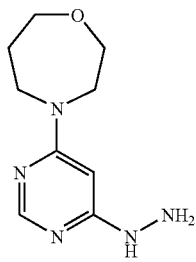

At RT, 8.8 ml (9.0 g, 180.2 mmol) of hydrazine hydrate are added dropwise with stirring to a solution of 3.9 g (18.0 mmol) of 4-(6-chloropyrimidin-4-yl)-1,4-oxazepane in 25 ml of ethanol. After 16 h of stirring at 80° C., the reaction solution is concentrated under reduced pressure. The residue is triturated with cold ethanol, the precipitated solid is filtered off and the filter residue is washed with 25 ml of diethyl ether. The product is dried under reduced pressure. Yield: 1.4 g (36% of theory)

HPLC (Method 11): R$_t$=2.48 min; MS (ESIpos): m/z=210 [M+H]$^+$;

$^1$H-NMR (400 MHz, DMSO-d$_6$): δ=7.91 (s, 1H), 7.56 (br. s, 1H), 5.81 (s, 1H), 4.12 (br. s, 2H), 3.75-3.55 (m, 8H), 1.85 (quintet, 2H).

Example 1

2-[6-(4-Cyclobutylpiperazin-1-yl)pyrimidin-4-yl]-4-(1H-imidazol-1-yl)-1,2-dihydro-3H-pyrazol-3-one

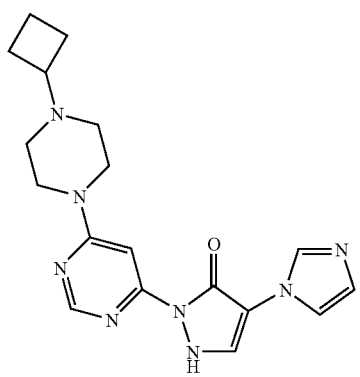

16 μl (23 mg, 0.2 mmol) of trifluoroacetic acid are added to a mixture of 211 mg (1.0 mmol) of the compound from Example 5A and 250 mg (1.0 mmol) of the compound from Example 9A in 4 ml of ethyl acetate, and the mixture is stirred at 100° C. for 20 h. The reaction mixture is concentrated under reduced pressure, more ethyl acetate and trifluoroacetic acid (the same amounts as above) are added and the mixture is stirred at 100° C. for 20 h. The reaction mixture is cooled to RT, and the precipitated solid is filtered off and washed with diethyl ether. The residue is pre-purified by column chromatography on silica gel (mobile phase dichloromethane/methanol/ammonia 10/2/0.2) and purified by preparative HPLC (RP18 column; mobile phase: acetonitrile/water gradient). Yield: 137 mg (36% of theory)

HPLC (Method 6): R$_t$=2.73 min; MS (ESIpos): m/z=367 [M+H]$^+$;

$^1$H-NMR (400 MHz, DMSO-d$_6$): δ=8.40 (s, 1H), 8.12 (s, 1H), 7.90 (s, 1H), 7.74 (s, 1H), 7.50 (s, 1H), 7.07 (s, 1H), 3.65-3.58 (m, 4H), 2.77 (quintet, 1H), 2.38-2.35 (m, 4H), 2.01-1.96 (m, 2H), 1.89-1.79 (m, 2H), 1.67-1.62 (m, 2H).

Example 2

2-[6-(4-Cyclobutylpiperazin-1-yl)pyrimidin-4-yl]-4-(1H-1,2,3-triazol-1-yl)-1,2-dihydro-3H-pyrazol-3-one

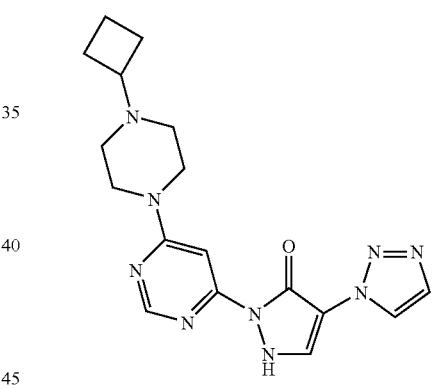

16 μl (23 mg, 0.2 mmol) of trifluoroacetic acid are added to a mixture of 211 mg (1.0 mmol) of the compound from Example 8A and 250 mg (1.0 mmol) of the compound from Example 9A in 4 ml of ethyl acetate, and the mixture is stirred at 100° C. for 20 h. The reaction mixture is concentrated under reduced pressure, more ethyl acetate and trifluoroacetic acid (the same amounts as above) are added and the mixture is stirred at 100° C. for 3 d. The reaction mixture is cooled to RT, and the precipitated solid is filtered off and washed with diethyl ether. The residue is suspended in 2 ml of water, dissolved by adding aqueous 1 N sodium hydroxide solution (pH=9-10) and purified by preparative HPLC (RP18 column; mobile phase: acetonitrile/water gradient). Yield: 195 mg (51% of theory)

HPLC (Method 6): R$_t$=2.90 min; MS (ESIpos): m/z=368 [M+H]$^+$;

$^1$H-NMR (400 MHz, DMSO-d$_6$): δ=8.41 (s, 1H), 8.40 (s, 1H), 7.88 (s, 1H), 7.82 (s, 1H), 7.75 (s, 1H), 3.70-3.65 (m, 4H), 3.03-2.97 (m, 1H), 2.60-2.57 (m, 4H), 2.06-2.02 (m, 2H), 1.98-1.90 (m, 2H), 1.70-1.64 (m, 2H).

Example 3

1-{2-[6-(4-Cyclobutylpiperazin-1-yl)pyrimidin-4-yl]-3-oxo-2,3-dihydro-1H-pyrazol-4-yl}-1H-imidazole-4-carbonitrile

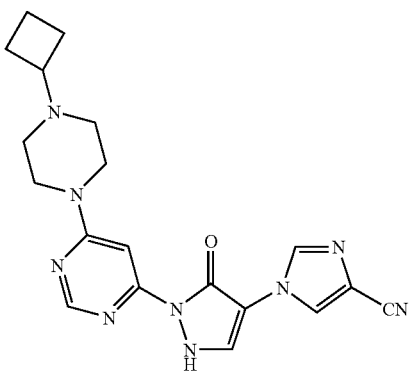

16 µl (23 mg, 0.2 mmol) of trifluoroacetic acid are added to a mixture of 236 mg (1.0 mmol) of the compound from Example 6A and 250 mg (1.0 mmol) of the compound from Example 9A in 4 ml of ethyl acetate, and the mixture is stirred at 100° C. for 20 h. The reaction mixture is concentrated under reduced pressure, more ethyl acetate and trifluoroacetic acid (the same amounts as above) are added and the mixture is stirred at 100° C. for 3 d. The reaction mixture is cooled to RT, and the precipitated solid is filtered off and washed with diethyl ether. The residue is suspended in 2 ml of water, dissolved by adding aqueous 1 N sodium hydroxide solution (pH=9-10) and purified by preparative HPLC (RP18 column; mobile phase: acetonitrile/water gradient). Yield: 219 mg (56% of theory)

HPLC (Method 6): $R_t$=3.10 min; MS (ESIpos): m/z=392 [M+H]$^+$;

$^1$H-NMR (400 MHz, DMSO-d$_6$): δ=8.38 (d, 1H), 8.37 (d, 1H), 8.17 (d, 1H), 7.82 (s, 1H), 7.80 (s, 1H), 3.68-3.62 (m, 4H), 3.38-3.30 (m, 4H), 2.96-2.91 (m, 1H), 2.06-2.00 (m, 2H), 1.95-1.85 (m, 2H), 1.70-1.63 (m, 2H).

Example 4

1-{2-[6-(3-Hydroxyazetidin-1-yl)pyrimidin-4-yl]-3-oxo-2,3-dihydro-1H-pyrazol-4-yl}-1H-imidazole-4-carbonitrile

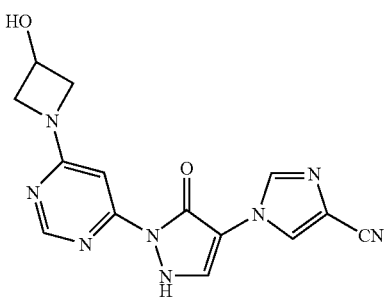

46 µl (68 mg, 0.6 mmol) of trifluoroacetic acid are added to a mixture of 700 mg (3.0 mmol) of the compound from Example 6A and 541 mg (3.0 mmol) of the compound from Example 10A in 10 ml of ethyl acetate, and the mixture is stirred at 100° C. for 10 h. The reaction mixture is concentrated under reduced pressure and taken up in 5 ml of ethanol, and the precipitate is filtered off. The solid is suspended in 10 ml of water, and 1 N aqueous sodium hydroxide solution (pH=9) is added until the solid is dissolved. The pH is then adjusted to 7 using 1 N hydrochloric acid, the mixture is concentrated to a volume of about 5 ml and the precipitate formed is filtered off. The residue is washed with water and diisopropyl ether and chromatographed by preparative HPLC (Method 8). The solid is then suspended in 10 ml of water, and 1 N aqueous sodium hydroxide solution (pH=9) is added until the solid is dissolved. The pH is then adjusted to 7 using 1 N hydrochloric acid, the mixture is concentrated to a volume of about 2.5 ml and the precipitate formed is filtered off. The filtrate is concentrated to about 2 ml and filtered again. Both residues are combined, washed with water and ethyl acetate and dried under reduced pressure. Yield: 78 mg (8% of theory)

HPLC (Method 6): $R_t$=2.90 min; MS (ESIpos): m/z=325 [M+H]$^+$;

$^1$H-NMR (400 MHz, DMSO-d$_6$): δ=8.35 (s, 1H), 8.29 (s, 1H), 8.17 (s, 1H), 7.66 (s, 1H), 7.34 (s, 1H), 5.80-5.75 (m, 1H), 4.63-4.58 (m, 1H), 4.24-4.20 (m, 2H), 3.75-3.73 (m, 2H).

Example 5

1-{6-[4-(1H-Imidazol-1-yl)-5-oxo-2,5-dihydro-1H-pyrazol-1-yl]pyrimidin-4-yl}azetidine-3-carboxylic acid

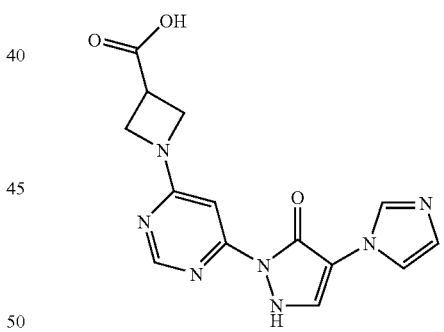

46 mg (0.3 mmol) of azetidine-3-carboxylic acid hydrochloride are initially charged in a mixture of 1 ml of water and 0.3 ml of ethanol. 100 mg (0.3 mmol) of the compound from Example 13A are added, and the mixture is stirred at 100° C. for 1 h. The reaction mixture is then adjusted to pH=7 using aqueous 1 N sodium hydroxide solution and stirred at 100° C. for 16 h. Once more, the mixture is adjusted to pH=7 using aqueous 1 N sodium hydroxide solution and reacted in a single mode microwave (Emrys Optimizer) at 150° C. for 1 h. The reaction mixture is concentrated under reduced pressure and purified by preparative HPLC (RP18 column; mobile phase: acetonitrile/water gradient). Yield: 23 mg (21% of theory)

LC-MS (Method 8): $R_t$=0.86 min; MS (ESIpos): m/z=328 [M+H]$^+$;

¹H-NMR (400 MHz, DMSO-d₆): δ=8.41 (s, 1H), 7.79 (s, 1H), 7.47 (s, 1H), 7.36 (s, 1H), 7.31 (s, 1H), 6.89 (s, 1H), 4.09 (t, 2H), 3.99 (t, 2H).

Example 6

1-{6-[5-Oxo-4-(1H-1,2,3-triazol-1-yl)-2,5-dihydro-1H-pyrazol-1-yl]pyrimidin-4-yl}azetidine-3-carboxylic acid

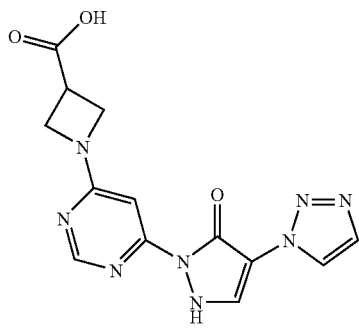

55 mg (0.4 mmol) of azetidine-3-carboxylic acid hydrochloride are initially charged in 2 ml of water. 100 mg (0.3 mmol) of the compound from Example 12A are added, and the pH is adjusted to 7 using aqueous 1 N sodium hydroxide solution. The mixture is reacted in a single mode microwave (Emrys Optimizer) at 150° C. for 1 h. The reaction mixture is concentrated under reduced pressure and purified by preparative HPLC (RP18 column; mobile phase: acetonitrile/water gradient). Yield: 15 mg (13% of theory)

HPLC (Method 6): $R_t$=2.81 min; MS (ESIpos): m/z=329 [M+H]⁺;

¹H-NMR (400 MHz, DMSO-d₆): δ=8.42 (s, 1H), 8.26 (s, 1H), 7.70 (s, 1H), 7.67 (s, 1H), 7.34 (s, 1H), 4.05-3.96 (m, 2H and 2H), 3.13-3.07 (m, 1H).

Example 7

4-(1H-Imidazol-1-yl)-2-[6-(3-methylazetidin-1-yl)pyrimidin-4-yl]-1,2-dihydro-3H-pyrazol-3-one

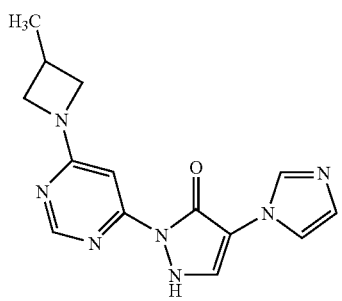

43 mg (0.4 mmol) of 3-methylazetidine hydrochloride, 100 mg (0.3 mmol) of the compound from Example 13A and 174 µl (130 mg, 1.0 mmol) of N-ethyl-N-(propan-2-yl)propane-2-amine are suspended in 2 ml of tetrahydrofuran and reacted in a single mode microwave (Emrys Optimizer) at 120° C. for 4.5 h. The reaction mixture is concentrated under reduced pressure, taken up in water with addition of aqueous 1 N sodium hydroxide solution (pH=9-10) and purified by preparative HPLC (RP18 column; mobile phase: acetonitrile/water gradient). Yield: 30 mg (30% of theory)

HPLC (Method 6): $R_t$=3.07 min; MS (ESIpos): m/z=298 [M+H]⁺;

¹H-NMR (400 MHz, DMSO-d₆): δ=8.25 (s, 1H), 7.81 (s, 1H), 7.46 (s, 1H), 7.39 (s, 1H), 7.31 (s, 1H), 6.88 (s, 1H), 4.10 (t, 2H), 3.54 (dd, 2H), 2.86-2.75 (m, 1H), 1.25 (d, 3H).

Example 8

2-[6-(3-Methylazetidin-1-yl)pyrimidin-4-yl]-4-(1H-1,2,3-triazol-1-yl)-1,2-dihydro-3H-pyrazol-3-one

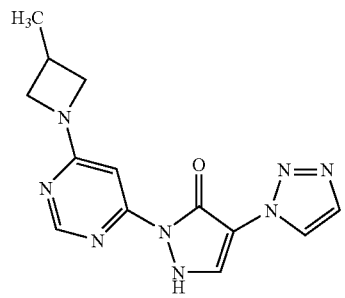

43 mg (0.4 mmol) of 3-methylazetidine hydrochloride, 100 mg (0.3 mmol) of the compound from Example 12A and 174 µl (130 mg, 1.0 mmol) of N-ethyl-N-(propan-2-yl)propane-2-amine are suspended in 2 ml of tetrahydrofuran and reacted in a single mode microwave (Emrys Optimizer) at 120° C. for 1.5 h. The reaction mixture is concentrated under reduced pressure, taken up in water with addition of aqueous 1 N sodium hydroxide solution (pH=9-10) and purified by preparative HPLC (RP18 column; mobile phase: acetonitrile/water gradient). Yield: 25 mg (25% of theory)

HPLC (Method 6): $R_t$=3.00 min; MS (ESIpos): m*z=299 [M+H]⁺;

¹H-NMR (400 MHz, DMSO-d₆): δ=8.41 (s, 1H), 8.27 (s, 1H), 7.70 (s, 1H), 7.67 (s, 1H), 7.41 (s, 1H), 4.11 (t, 2H), 3.56 (dd, 2H), 2.86-2.78 (m, 1H), 1.25 (d, 3H).

Example 9

2-{6-[3-(Dimethylamino)azetidin-1-yl]pyrimidin-4-yl}-4-(1H-1,2,3-triazol-1-yl)-1,2-dihydro-3H-pyrazol-3-one dihydrochloride

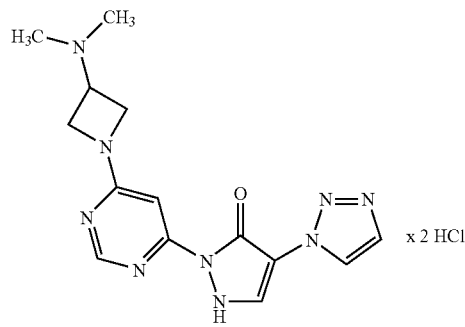

271 mg (1.5 mmol) of N,N-dimethylazetidine-3-amine dihydrochloride, 400 mg (1.5 mmol) of the compound from Example 12A and 847 mg (6.1 mmol) of potassium carbonate are suspended in 8 ml of N,N-dimethylformamide and stirred at 100° C. for 16 h. The reaction mixture is concentrated under reduced pressure and purified by preparative HPLC (RP18 column; mobile phase: acetonitrile/water gradient with addition of 0.1% strength trifluoroacetic acid). Further purification is carried out by preparative HPLC (RP18 column; mobile phase: acetonitrile/water gradient with addition of 0.1% strength formic acid). 2 ml of 1 N hydrochloric acid is added to the product-containing fractions, and the mixture is stirred at RT for 1 h. The solid is filtered off and dried under high vacuum. Yield: 62 mg (17% of theory)

LC-MS (Method 5): $R_t$=0.19 min; MS (ESIpos): m/z=328 [M+H]$^+$;

$^1$H-NMR (400 MHz, DMSO-d$_6$): δ=8.42 (s, 1H), 8.28 (s, 1H), 7.69 (s, 1H), 7.66 (s, 1H), 7.52 (s, 1H), 4.02 (t, 2H), 3.76 (dd, 2H), 3.24-3.18 (m, 1H), 2.12 (s, 6H).

Example 10

2-[6-(4,4-Difluoropiperidin-1-yl)pyrimidin-4-yl]-4-(1H-imidazol-1-yl)-1,2-dihydro-3H-pyrazol-3-one

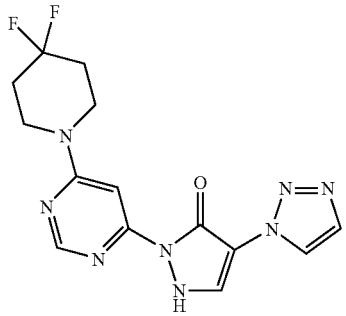

100 mg (0.3 mmol) of the compound from Example 13A, 63 mg (0.4 mmol) of 4,4-difluoropiperidine hydrochloride and 116 μl (86 mg, 0.7 mmol) of N-ethyl-N-(propan-2-yl)propane-2-amine are initially charged in 2 ml of tetrahydrofuran and reacted in a single mode microwave (Emrys Optimizer) at 120° C. for 2.5 h. After concentration under reduced pressure, the residue is taken up in acetonitrile/water and purified by preparative HPLC (RP18 column; mobile phase: acetonitrile/water gradient). Yield: 82 mg (71% of theory)

HPLC (Method 6): $R_t$=3.37 min; MS (ESIpos): m/z=348 [M+H]$^+$;

$^1$H-NMR (400 MHz, DMSO-d$_6$): δ=8.49 (s, 1H), 8.38 (s, 1H), 8.15 (s, 1H), 7.76 (s, 1H), 7.64 (s, 1H), 7.22 (s, 1H), 3.80 (t, 4H), 2.06 (heptet, 4H).

Example 11

2-[6-(4,4-Difluoropiperidin-1-yl)pyrimidin-4-yl]-4-(1H-1,2,3-triazol-1-yl)-1,2-dihydro-3H-pyrazol-3-one

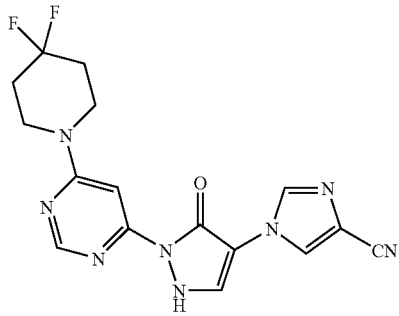

250 mg (0.8 mmol) of the compound from Example 12A, 158 mg (1.0 mmol) of 4,4-difluoropiperidine hydrochloride and 435 μl (323 mg, 2.5 mmol) of N-ethyl-N-(propan-2-yl)propane-2-amine are initially charged in 5 ml of tetrahydrofuran and reacted in a single mode microwave (Emrys Optimizer) at 120° C. for 30 min. After pre-purification by preparative HPLC (RP18 column; mobile phase: acetonitrile/water gradient), the product is additionally purified by column chromatography on silica gel (mobile phase dichloromethane/methanol, 10/1). Yield: 29 mg (10% of theory)

HPLC (Method 6): $R_t$=3.49 min; MS (ESIpos): m/z=349 [M+H]$^+$;

$^1$H-NMR (400 MHz, DMSO-d$_6$): δ=8.56 (s, 1H), 8.39 (s, 1H), 8.30 (s, 1H), 7.87 (s, 1H), 7.57 (s, 1H), 3.91-3.81 (m, 4H), 2.09 (heptet, 4H).

Example 12

1-{2-[6-(4,4-Difluoropiperidin-1-yl)pyrimidin-4-yl]-3-oxo-2,3-dihydro-1H-pyrazol-4-yl}-1H-imidazole-4-carbonitrile A mixture of 200 mg (1.4 mmol) of the compound from Example 11A, 262 mg (1.7 mmol) of 4,4-difluoropiperidine hydrochloride and 289 μl (215 mg, 1.7 mmol) of N-ethyl-N-(propan-2-yl)propane-2-amine in 3 ml of water is stirred at 100° C. for 16 h. Following the addition of 53 μl (79 mg, 0.7 mmol) of trifluoroacetic acid and 324 mg (1.4 mmol) of the compound from Example 6A, the reaction mixture is stirred at 100° C. for 16 h. The precipitated solid is filtered off and washed first with water and then with diethyl ether. The product is dried under reduced pressure. Yield: 111 mg (21% of theory)

LC-MS (Method 4): $R_t$=1.69 min; MS (ESIpos): m/z=373 [M+H]$^+$;

$^1$H-NMR (400 MHz, DMSO-d$_6$): δ=8.55 (s, 1H), 8.44 (d, 1H), 8.33 (s, 1H), 8.22 (d, 1H), 7.60 (br. s, 1H), 3.84 (br. s, 4H), 2.09 (heptet, 4H).

Example 13

1-{2-[6-(4,4-Difluoropiperidin-1-yl)pyrimidin-4-yl]-3-oxo-2,3-dihydro-1H-pyrazol-4-yl}-1H-1,2,3-triazole-4-carbonitrile

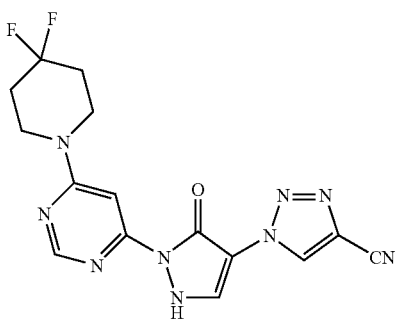

A mixture of 200 mg (1.4 mmol) of the compound from Example 11A, 262 mg (1.7 mmol) of 4,4-difluoropiperidine hydrochloride and 289 μl (215 mg, 1.7 mmol) of N-ethyl-N-(propan-2-yl)propane-2-amine in 3 ml of water is stirred at 100° C. for 16 h. Following the addition of 53 μl (79 mg, 0.7 mmol) of trifluoroacetic acid and 325 mg (1.4 mmol) of the compound from Example 7A, the reaction mixture is stirred at 100° C. for 16 h. The precipitated solid is filtered off and washed first with water and then with diethyl ether. The product is dried under reduced pressure. Yield: 34 mg (7% of theory)

LC-MS (Method 4): $R_t$=1.77 min; MS (ESIpos): m/z=374 [M+H]$^+$;

$^1$H-NMR (400 MHz, DMSO-d$_6$): δ=9.24 (s, 1H), 8.59 (s, 1H), 8.27 (s, 1H), 7.54 (s, 1H), 3.90 (br. s, 4H), 2.12 (heptet, 4H).

Example 14

2-[6-(3,3-Difluoropyrrolidin-1-yl)pyrimidin-4-yl]-4-(1H-imidazol-1-yl)-1,2-dihydro-3H-pyrazol-3-one

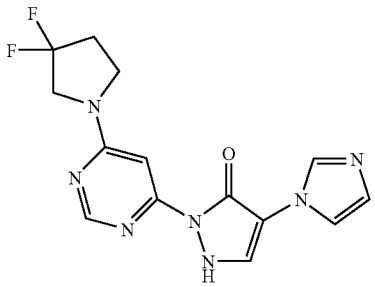

100 mg (0.3 mmol) of the compound from Example 13A, 58 mg (0.4 mmol) of 3,3-difluoropyrrolidine hydrochloride and 175 μl (130 mg, 1.0 mmol) of N-ethyl-N-(propan-2-yl)propane-2-amine are initially charged in 2 ml of tetrahydrofuran and reacted in a single mode microwave (Emrys Optimizer) at 120° C. for 1 h. After concentration under reduced pressure, the residue is taken up in acetonitrile/water and purified by preparative HPLC (RP18 column; mobile phase: acetonitrile/water gradient). Yield: 111 mg (99% of theory)

HPLC (Method 6): $R_t$=3.18 min; MS (ESIpos): m/z=334 [M+H]$^+$;

$^1$H-NMR (400 MHz, methanol-d$_4$): δ=8.41 (s, 1H), 7.85 (s, 1H), 7.62 (s, 1H), 7.56 (s, 1H), 7.29 (s, 1H), 7.03 (s, 1H), 3.91 (t, 2H), 3.76 (t, 2H), 2.55 (heptet, 2H).

Example 15

2-[6-(3,3-Difluoropyrrolidin-1-yl)pyrimidin-4-yl]-4-(1H-1,2,3-triazol-1-yl)-1,2-dihydro-3H-pyrazol-3-one

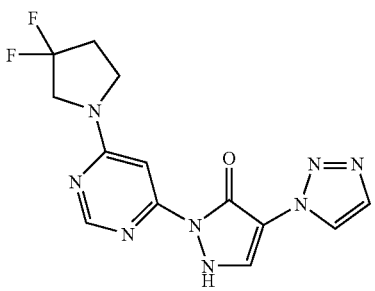

100 mg (0.8 mmol) of the compound from Example 12A, 57 mg (0.4 mmol) of 3,3-difluoropyrrolidine hydrochloride and 174 μl (129 mg, 1.0 mmol) of N-ethyl-N-(propan-2-yl)propane-2-amine were initially charged in 2 ml of tetrahydrofuran and reacted in a single mode microwave (Emrys Optimizer) at 120° C. for 30 min. After concentration under reduced pressure, the residue is taken up in acetonitrile/water and purified by preparative HPLC (RP18 column; mobile phase: acetonitrile/water gradient). Yield: 13 mg (12% of theory)

HPLC (Method 6): $R_t$=3.33 min; MS (ESIpos): m/z=335 [M+H]$^+$;

$^1$H-NMR (400 MHz, DMSO-d$_6$): δ=8.42 (s, 1H), 8.35 (s, 1H), 7.72-7.66 (m, 3H), 3.87 (t, 2H), 3.65 (t, 2H), 2.64-2.50 (m, partially beneath the DMSO signal, 2H).

Example 16

1-{2-[6-(3,3-Difluoropyrrolidin-1-yl)pyrimidin-4-yl]-3-oxo-2,3-dihydro-1H-pyrazol-4-yl}-1H-imidazole-4-carbonitrile

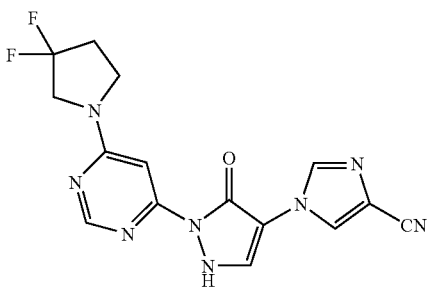

A mixture of 200 mg (1.4 mmol) of the compound from Example 11A, 238 mg (1.7 mmol) of 3,3-difluoropyrrolidine hydrochloride and 289 µl (215 mg, 1.7 mmol) of N-ethyl-N-(propan-2-yl)propane-2-amine in 3 ml of water is stirred at 100° C. for 16 h. Following the addition of 53 µl (79 mg, 0.7 mmol) of trifluoroacetic acid and 324 mg (1.4 mmol) of the compound from Example 6A, the reaction mixture is stirred at 100° C. for 16 h. 1 ml of 1 N hydrochloric acid is added to the reaction mixture. The resulting precipitated hydrochloride of the crude product is filtered off, washed with diethyl ether and dried. The crude product still contains unreacted starting material (compound from Example 11A). Accordingly, the crude product is reacted with 108 µl (80 mg, 0.6 mmol) of N-ethyl-N-(propan-2-yl)propane-2-amine, 10 mg (0.1 mmol) of 3,3-difluoropyrrolidine hydrochloride and 2 ml of water in a single mode microwave (Emrys Optimizer) at 170° C. for 15 min. The reaction solution purified by preparative HPLC (RP18 column; mobile phase: acetonitrile/water gradient). Yield: 30 mg (6% of theory)

LC-MS (Method 4): $R_t$=1.58 min; MS (ESIpos): m/z=359 [M+H]$^+$;

$^1$H-NMR (400 MHz, DMSO-d$_6$): δ=8.55 (s, 1H), 8.44 (d, 1H), 8.33 (s, 1H), 8.21 (d, 1H), 7.26 (br. s, 1H), 3.99 (t, 2H), 3.75 (br. s, 2H), 2.66-2.54 (m, partially beneath the DMSO signal, 2H).

Example 17

1-{2-[6-(3,3-Difluoropyrrolidin-1-yl)pyrimidin-4-yl]-3-oxo-2,3-dihydro-1H-pyrazol-4-yl}-1H-1,2,3-triazole-4-carbonitrile

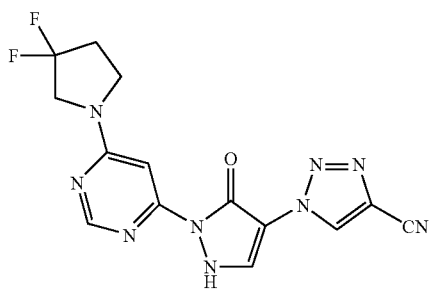

A mixture of 200 mg (1.4 mmol) of the compound from Example 11A, 238 mg (1.7 mmol) of 3,3-difluoropyrrolidine hydrochloride and 289 µl (215 mg, 1.7 mmol) of N-ethyl-N-(propan-2-yl)propane-2-amine in 3 ml of water is stirred at 100° C. for 16 h. Following the addition of 53 µl (79 mg, 0.7 mmol) of trifluoroacetic acid and 325 mg (1.4 mmol) of the compound from Example 7A, the reaction mixture is stirred at 100° C. for 16 h. The precipitated solid is filtered off and washed first with water and then with diethyl ether. The product is dried under reduced pressure. Yield: 137 mg (27% of theory)

LC-MS (Method 4): $R_t$=1.66 min; MS (ESIpos): m/z=360 [M+H]$^+$;

$^1$H-NMR (400 MHz, DMSO-d$_6$): δ=9.25 (s, 1H), 8.61 (s, 1H), 8.29 (s, 1H), 7.21 (br. s, 1H), 4.06 (t, 2H), 3.82 (br. s, 2H), 2.69-2.55 (m, partially beneath the DMSO signal, 2H).

Example 18

2-[6-(3,3-Difluoroazetidin-1-yl)pyrimidin-4-yl]-4-(1H-imidazol-1-yl)-1,2-dihydro-3H-pyrazol-3-one

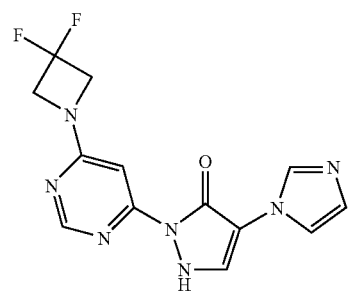

100 mg (0.3 mmol) of the compound from Example 13A, 52 mg (0.4 mmol) of 3,3-difluoroazetidine hydrochloride and 175 µl (130 mg, 1.0 mmol) of N-ethyl-N-(propan-2-yl)propane-2-amine are initially charged in 2 ml of tetrahydrofuran and reacted in a single mode microwave (Emrys Optimizer) at 120° C. for 3 h. The precipitated solid is filtered off and the filtrate is concentrated under reduced pressure. The residue is taken up in acetonitrile/water and purified by preparative HPLC (RP18 column; mobile phase: acetonitrile/water gradient). Yield: 36 mg (32% of theory)

HPLC (Method 6): $R_t$=3.00 min; MS (ESIpos): m/z=320 [M+H]$^+$;

$^1$H-NMR (400 MHz, DMSO-d$_6$): δ=8.42 (s, 1H), 8.16 (s, 1H), 7.79 (s, 1H), 7.56 (s, 1H), 7.50 (s, 1H), 7.07 (s, 1H), 4.49 (t, 4H).

Example 19

2-[6-(3,3-Difluoroazetidin-1-yl)pyrimidin-4-yl]-4-(1H-1,2,3-triazol-1-yl)-1,2-dihydro-3H-pyrazol-3-one

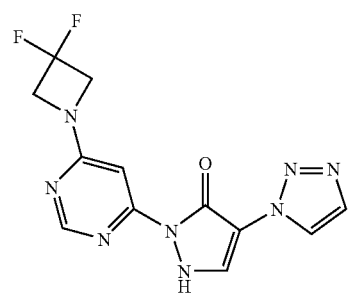

100 mg (0.3 mmol) of the compound from Example 12A, 52 mg (0.4 mmol) of 3,3-difluoroazetidine hydrochloride and 174 µl (130 mg, 1.0 mmol) of N-ethyl-N-(propan-2-yl)propane-2-amine are initially charged in 2 ml of tetrahydrofuran and reacted in a single mode microwave (Emrys Optimizer) at 120° C. for 30 min. After concentration under reduced pressure, the residue is taken up in acetonitrile/water and purified by preparative HPLC (RP18 column; mobile phase: acetonitrile/water gradient). Yield: 36 mg (34% of theory)

HPLC (Method 6): $R_t$=3.20 min; MS (ESIpos): m/z=321 [M+H]$^+$;

$^1$H-NMR (400 MHz, DMSO-$d_6$): δ=8.42 (s, 1H), 8.39 (s, 1H), 7.71 (s, 2H), 7.62 (s, 1H), 4.46 (t, 4H).

Example 20

1-{2-[6-(3,3-Difluoroazetidin-1-yl)pyrimidin-4-yl]-3-oxo-2,3-dihydro-1H-pyrazol-4-yl}-1H-imidazole-4-carbonitrile

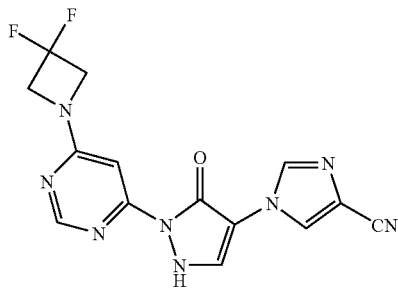

A mixture of 120 mg (0.8 mmol) of the compound from Example 11A, 129 mg (1.0 mmol) of 3,3-difluoroazetidine hydrochloride and 174 μl (129 mg, 1.0 mmol) of N-ethyl-N-(propan-2-yl)propane-2-amine in 3 ml of water is stirred at 100° C. for 16 h. Following the addition of 32 μl (47 mg, 0.4 mmol) of trifluoroacetic acid and 194 mg (0.8 mmol) of the compound from Example 6A, the reaction mixture is stirred at 100° C. for 16 h. The precipitated solid is filtered off and washed first with water and then with diethyl ether. The product is dried under reduced pressure. Yield: 32 mg (11% of theory)

LC-MS (Method 4): $R_t$=1.48 min; MS (ESIpos): m/z=345 [M+H]$^+$;

$^1$H-NMR (400 MHz, DMSO-$d_6$): δ=8.80-8.08 (m, 4H), 7.25 (s, 1H), 4.61 (br. s, 4H).

Example 21

1-{2-[6-(3,3-Difluoroazetidin-1-yl)pyrimidin-4-yl]-3-oxo-2,3-dihydro-1H-pyrazol-4-yl}-1H-1,2,3-triazole-4-carbonitrile

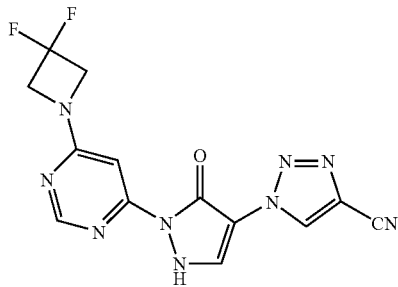

A mixture of 120 mg (0.8 mmol) of the compound from Example 11A, 129 mg (1.0 mmol) of 3,3-difluoroazetidine hydrochloride and 174 μl (129 mg, 1.0 mmol) of N-ethyl-N-(propan-2-yl)propane-2-amine in 3 ml of water is stirred at 100° C. for 16 h. Following the addition of 32 μl (47 mg, 0.4 mmol) of trifluoroacetic acid and 194 mg (0.8 mmol) of the compound from Example 7A, the reaction mixture is stirred at 100° C. for 16 h. The precipitated solid is filtered off and washed first with water and then with diethyl ether. The product is dried under reduced pressure. Yield: 51 mg (18% of theory)

LC-MS (Method 4): $R_t$=1.56 min; MS (ESIpos): m/z=346 [M+H]$^+$;

$^1$H-NMR (400 MHz, DMSO-$d_6$): δ=9.26 (s, 1H), 8.60 (s, 1H), 8.36 (s, 1H), 7.18 (s, 1H), 4.69 (t, 4H).

Example 22

4-(1H-Imidazol-1-yl)-2-[6-(1,4-oxazepan-4-yl)pyrimidin-4-yl]-1,2-dihydro-3H-pyrazol-3-one hydrochloride

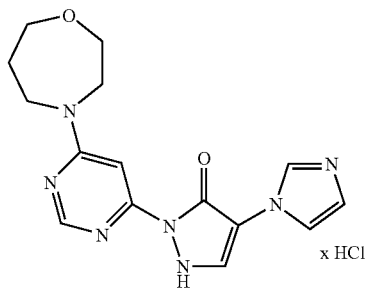

A mixture of 200 mg (1.0 mmol) of the compound from Example 5A, 200 mg (1.0 mmol) of the compound from Example 14A and 37 μl (54 mg, 0.5 mmol) of trifluoroacetic acid in 3 ml of water is stirred at 100° C. for 16 h. After pre-purification by preparative HPLC (RP18 column; mobile phase: acetonitrile/water gradient), the crude product is stirred with 1 ml of 1 N hydrochloric acid, filtered off and washed with diethyl ether. The product is dried under reduced pressure. Yield: 21 mg (6% of theory)

LC-MS (Method 4): $R_t$=0.95 min; MS (ESIpos): m/z=364 [M+H]$^+$;

$^1$H-NMR (400 MHz, DMSO-$d_6$): δ=9.46 (s, 1H), 8.56 (s, 1H), 8.30 (s, 1H), 8.06 (t, 1H), 7.83 (t, 1H), 7.50-7.33 (m, 1H), 4.05 (br. s, 2H), 3.91-3.70 (m, 4H), 3.68 (t, 2H), 2.04-1.73 (m, 2H).

Example 23

2-[6-(1,4-Oxazepan-4-yl)pyrimidin-4-yl]-4-(1H-1,2,3-triazol-1-yl)-1,2-dihydro-3H-pyrazol-3-one hydrochloride

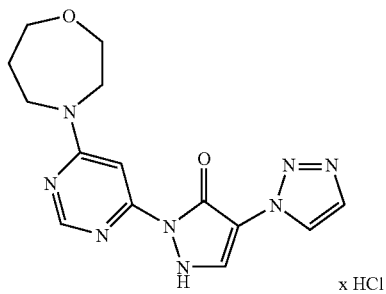

A mixture of 400 mg (1.3 mmol) of the compound from Example 12A and 220 mg (1.6 mmol) of 1,4-oxazepane hydrochloride in 4 ml of propan-2-ol is reacted in a single mode microwave (Emrys Optimizer) at 115° C. for 30 min. 232 μl (172 mg, 1.3 mmol) of N-ethyl-N-(propan-2-yl)propane-2-amine are added, and the reaction mixture is reacted in a single mode microwave (Emrys Optimizer) at 115° C. for 20 min. After concentration under reduced pressure, the residue is taken up in acetonitrile/water/trifluoroacetic acid and chromatographed by preparative HPLC (Method 9). The trifluoroacetate salt obtained from the HPLC separation is lyophilized andconverted into the hydrochloride using 2 ml of 1 N hydrochloric acid. Yield: 7 mg (1% of theory)

LC-MS (Method 4): $R_t$=1.20 min; MS (ESIpos): m/z=329 [M+H]$^+$;

$^1$H-NMR (400 MHz, DMSO-d$_6$): δ=8.54 (s, 1H), 8.38 (s, 1H), 8.25 (s, 1H), 7.86 (d, 1H), 7.35 (br. s, 1H), 4.14-3.69 (m, 6H), 3.67 (t, 2H), 2.03-1.77 (m, 2H).

Example 24

2-[6-(1,4-Oxazepan-4-yl)pyrimidin-4-yl]-4-(1H-1,2,3-triazol-1-yl)-1,2-dihydro-3H-pyrazol-3-one

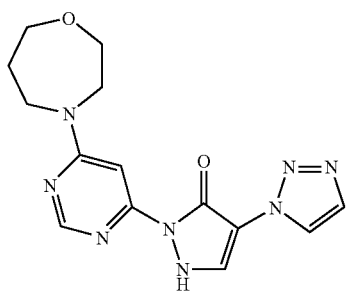

A mixture of 500 mg (1.7 mmol) of the compound from Example 12A, 688 mg (5.0 mmol) of 1,4-oxazepane hydrochloride and 1.4 ml (1077 mg, 8.3 mmol) of N-ethyl-N-(propan-2-yl)propane-2-amine is reacted in 10 ml of tetrahydrofuran/ethanol (1/1) in a single mode microwave (Emrys Optimizer) at 140° C. for 30 min. After pre-purification by preparative HPLC (RP18 column; mobile phase: acetonitrile/water gradient), the crude product is taken up in acetonitrile/trifluoroacetic acid and chromatographed by preparative HPLC (Method 10). The trifluoroacetate salt obtained from the HPLC separation is lyophilized and adjusted to pH=7-8 using 1 N aqueous sodium hydroxide solution. The product is isolated by preparative HPLC (RP18 column; mobile phase: acetonitrile/water gradient). Yield: 176 mg (31% of theory)

LC-MS (Method 4): $R_t$=1.19 min; MS (ESIpos): m/z=329 [M+H]$^+$;

$^1$H-NMR (400 MHz, DMSO-d$_6$): δ=8.41 (d, 1H), 8.33 (d, 1H), 7.78 (br. s, 1H), 7.72-7.70 (m, 2H), 3.91-3.65 (m, 6H), 3.62 (t, 2H), 1.95-1.83 (m, 2H).

Example 25

1-{2-[6-(1,4-Oxazepan-4-yl)pyrimidin-4-yl]-3-oxo-2,3-dihydro-1H-pyrazol-4-yl}-1H-imidazole-4-carbonitrile

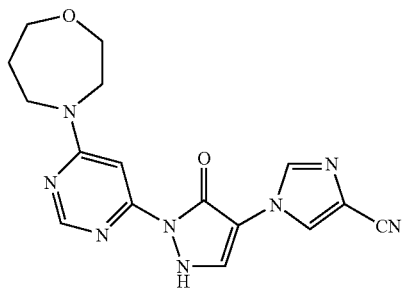

A mixture of 200 mg (0.9 mmol) of the compound from Example 6A, 178 mg (0.9 mmol) of the compound from Example 14A and 33 μl (49 mg, 0.4 mmol) of trifluoroacetic acid in 3 ml of water is stirred at 100° C. for 16 h. The precipitated solid is filtered off and washed first with water and then with diethyl ether. The product is dried under reduced pressure. Yield: 120 mg (40% of theory)

HPLC (Method 6): $R_t$=3.27 min; MS (ESIpos): m/z=353 [M+H]$^+$;

$^1$H-NMR (400 MHz, DMSO-d$_6$): δ=8.52 (s, 1H), 8.42 (d, 1H), 8.25 (s, 1H), 8.19 (d, 1H), 7.39 (br. s, 1H), 4.14-3.70 (m, 6H), 3.66 (t, 2H), 2.05-1.68 (m, 2H).

Example 26

1-{2-[6-(1,4-Oxazepan-4-yl)pyrimidin-4-yl]-3-oxo-2,3-dihydro-1H-pyrazol-4-yl}-1H-1,2,3-triazole-4-carbonitrile

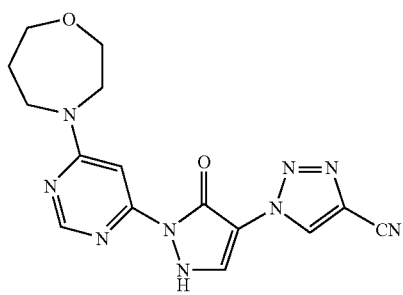

A mixture of 200 mg (0.9 mmol) of the compound from Example 7A, 178 mg (0.9 mmol) of the compound from Example 14A and 33 μl (49 mg, 0.4 mmol) of trifluoroacetic acid in 3 ml of water is stirred at 100° C. for 16 h. The precipitated solid is filtered off and washed first with water and then with diethyl ether. The product is dried under reduced pressure. Yield: 80 mg (27% of theory)

LC-MS (Method 4): $R_t$=1.40 min; MS (ESIpos): m/z=354 [M+H]$^+$;

¹H-NMR (400 MHz, DMSO-d₆): δ=9.22 (s, 1H), 8.56 (s, 1H), 8.21 (s, 1H), 7.45-7.26 (m, 1H), 4.06 (br. s, 2H), 3.92-3.71 (m, 4H), 3.68 (t, 2H), 2.06-1.74 (m, 2H).

Example 27

2-[6-(1,2-Oxazinan-2-yl)pyrimidin-4-yl]-4-(1H-1,2,3-triazol-1-yl)-1,2-dihydro-3H-pyrazol-3-one

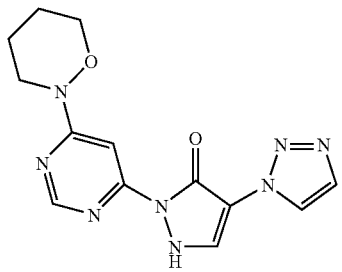

A mixture of 200 mg (0.7 mmol) of the compound from Example 12A, 99 mg (0.8 mmol) of 1,2-oxazinane hydrochloride [Bhat et al., *J. Chem. Soc. Perkin Trans.* 2 2000, 7, 1435-1446] and 348 μl (258 mg, 2.0 mmol) of N-ethyl-N-(propan-2-yl)propane-2-amine in 4 ml of tetrahydrofuran is reacted at 140° C. in a single mode microwave (Emrys Optimizer) for 30 min. After pre-purification by preparative HPLC (RP18 column; mobile phase: acetonitrile/water gradient), the crude product is taken up in acetonitrile/water/methanol and chromatographed by preparative HPLC (Method 11). The formate salt obtained from the HPLC separation is lyophilized and adjusted to pH=7-8 using 1 N aqueous sodium hydroxide solution. The product is isolated by preparative HPLC (RP18 column; mobile phase: acetonitrile/water gradient). Yield: 23 mg (11% of theory)

LC-MS (Method 4): $R_t$=1.38 min; MS (ESIpos): m/z=315 [M+H]⁺;

¹H-NMR (400 MHz, DMSO-d₆): δ=8.58 (d, 1H), 8.42 (d, 1H), 8.40 (br. s, 1H), 7.88 (d, 1H), 7.66 (br. s, 1H), 4.09 (t, 2H), 3.98 (t, 2H), 1.86-1.68 (m, 4H).

Example 28

1-{2-[6-(1,2-Oxazinan-2-yl)pyrimidin-4-yl]-3-oxo-2,3-dihydro-1H-pyrazol-4-yl}-1H-imidazole-4-carbonitrile

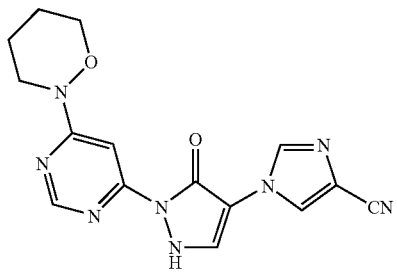

A mixture of 200 mg (1.4 mmol) of the compound from Example 11A, 205 mg (1.7 mmol) of 1,2-oxazinane hydrochloride [Bhat et al., *J. Chem. Soc. Perkin Trans.* 2 2000, 7, 1435-1446] and 289 μl (215 mg, 1.7 mmol) of N-ethyl-N-(propan-2-yl)propane-2-amine in 3 ml of water is stirred at 100° C. for 1.5 h. Following the addition of 59 μl (49 mg, 0.4 mmol) of trifluoroacetic acid and 324 mg (1.4 mmol) of the compound from Example 6A, the reaction mixture is stirred at 100° C. for 16 h. The precipitated solid is filtered off and washed first with water and then with diethyl ether. The product is dried under reduced pressure. Yield: 199 mg (39% of theory)

LC-MS (Method 5): $R_t$=0.87 min; MS (ESIpos): m/z=339 [M+H]⁺;

¹H-NMR (400 MHz, DMSO-d₆): δ=8.57 (d, 1H), 8.45 (d, 1H), 8.40 (br. s, 1H), 8.23 (d, 1H), 7.70 (br. s, 1H), 4.07 (t, 2H), 3.96 (t, 2H), 1.85-1.65 (m, 4H).

Example 29

1-{2-[6-(1,2-Oxazinan-2-yl)pyrimidin-4-yl]-3-oxo-2,3-dihydro-1H-pyrazol-4-yl}-1H-1,2,3-triazole-4-carbonitrile

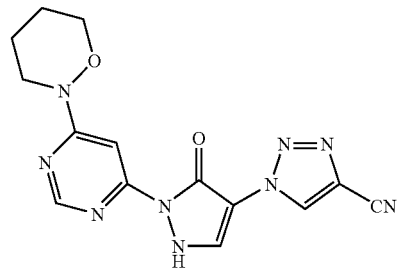

A mixture of 200 mg (1.4 mmol) of the compound from Example 11A, 205 mg (1.7 mmol) of 1,2-oxazinane hydrochloride [Bhat et al., *J. Chem. Soc. Perkin Trans.* 2 2000, 7, 1435-1446] and 289 μl (215 mg, 1.7 mmol) of N-ethyl-N-(propan-2-yl)propane-2-amine in 3 ml of water is stirred at 100° C. for 1.5 h. Following the addition of 59 μl (49 mg, 0.4 mmol) of trifluoroacetic acid and 325 mg (1.4 mmol) of the compound from Example 7A, the reaction mixture is stirred at 100° C. for 16 h. The precipitated solid is filtered off and washed first with water and then with diethyl ether. The product is dried under reduced pressure. Yield: 122 mg (24% of theory)

LC-MS (Method 4): $R_t$=1.66 min; MS (ESIpos): m/z=340 [M+H]⁺;

¹H-NMR (400 MHz, DMSO-d₆): δ=9.28 (s, 1H), 8.58 (s, 1H), 8.36 (s, 1H), 7.60 (br. s, 1H), 4.12 (t, 2H), 4.03 (t, 2H), 1.88-1.70 (m, 4H).

B. Evaluation of the Pharmacological Activity

The pharmacological properties of the compounds according to the invention can be demonstrated in the following assays:

| Abbreviations: | |
| --- | --- |
| DMEM | Dulbecco's modified Eagle medium |
| FCS | fetal calf serum |
| TMB | 3,3',5,5'-tetramethylbenzidine |
| Tris | tris(hydroxymethyl)aminomethane |

1. In Vitro Tests for Determination of the Activity and Selectivity of HIF Prolyl 4-hydroxylase Inhibitors 1.a) Inhibition of the Activity of HIF Prolyl Hydroxylase:

Hydroxylated HIF bonds specifically to the von Hippel-Lindau protein-elongin B-elongin C complex (VBC complex). This interaction occurs only if HIF is hydroxylated on a conserved prolyl radical. It is the basis for the biochemical determination of HIF prolyl hydroxylase activity. The test is carried out as described [Oehme F., Jonghaus W., Narouz-Ott L., Huetter J., Flamme I., *Anal. Biochem.* 330 (1), 74-80 (2004)]:

A clear 96-well microtiter plate coated with NeutrAvidin HBC (Pierce) is incubated with blocker casein for 30 minutes. The plate is then washed three times with 200 µl each time of wash buffer (50 mM Tris, pH 7.5, 100 mM NaCl, 10% (v/v) blocker casein, 0.05% (v/v) Tween 20) per well. The peptide biotin-DLDLEMLAPYIPMDDDFQL (Eurogentec, 4102 Seraing, Belgium) is added in a concentration of 400 nM in 100 µl wash buffer. This peptide serves as a substrate for the prolyl hydroxylation and is bonded to the microtiter plate. After incubation for 60 minutes, the plate is washed three times with wash buffer, incubated with 1 mM biotin in blocker casein for 30 minutes and then washed again three times with wash buffer.

To carry out the prolyl hydroxylase reaction, the peptide substrate bonded to the plate is incubated with a cell lysate containing prolyl hydroxylase for 1 to 60 minutes. The reaction takes place in 100 µl reaction buffer (20 mM Tris, pH 7.5, 5 mM KCl, 1.5 mM $MgCl_2$, 1 µM-1 mM 2-oxoglutarate, 10 µM $FeSO_4$, 2 mM ascorbate) at room temperature. The reaction mixture moreover contains various concentrations of the prolyl hydroxylase inhibitor to be tested. The test substance is preferably, but not exclusively, employed at concentrations of between 1 nM and 100 µM. The reaction is stopped by washing the plate three times with wash buffer.

For quantitative determination of the prolyl hydroxylation, a fusion protein which contains both thioredoxin from *E. coli* and the VBC complex in 80 µl bonding buffer (50 mM Tris, pH 7.5, 120 mM NaCl) is added. After 15 minutes, 10 µl of a solution of polyclonal anti-thioredoxin antibodies from rabbit in bonding buffer are added. After a further 30 minutes, 10 µl of a solution of anti-rabbit immunoglobulin coupled to horseradish peroxidase in bonding buffer are added. After incubation at room temperature for 30 minutes, the plate is washed three times with wash buffer in order to remove non-bonded VBC complex and antibodies. To determine the amount of bonded VBC complex, the plate is incubated with TMB for 15 minutes. The colour reaction is ended by addition of 100 µl 1 M sulphuric acid. The amount of bonded VBC complex is determined by measurement of the optical density at 450 nm. It is proportional to the amount of hydroxylated proline in the peptide substrate.

Alternatively, a VBC complex coupled to europium (Perkin Elmer) can be used for detection of the prolyl hydroxylation. In this case, the amount of bonded VBC complex is determined by the fluorescence with respect to time. The use of VBC complex labelled with [$^{35}$S]-methionine is moreover possible. For this, the radioactively labelled VBC complex can be prepared by in vitro transcription-translation in reticulocyte lysate.

The embodiment examples inhibit the activity of HIF prolyl hydroxylase in this test with an $IC_{50}$ value of $\leq 30$ µM. Representative $IC_{50}$ values for the embodiment examples are reproduced in the following Table 1:

TABLE 1

| Example No. | $IC_{50}$ [nM] |
|---|---|
| 2 | 880 |
| 5 | 540 |
| 9 | 760 |
| 17 | 130 |
| 20 | 90 |
| 21 | 70 |
| 25 | 180 |
| 26 | 380 |
| 29 | 170 |

1.b) Cellular, Functional In Vitro Test:

The activity of the compounds according to the invention is quantified with the aid of a recombinant cell line. The cell is originally derived from a human lung carcinoma cell line (A549, ATCC: American Type Culture Collection, Manassas, Va. 20108, USA). The test cell line is transfected in a stable manner with a vector which contains the reporter gene of *Photinus pyralis* luciferase (called luciferase in the following) under the control of an artificial minimal promoter. The minimal promoter comprises two hypoxia-responsible elements upstream of a TATA box [Oehme F., Ellinghaus P., Kolkhof P., Smith T. J., Ramakrishnan S., Hütter J., Schramm M., Flamme I., *Biochem. Biophys. Res. Commun.* 296 (2), 343-9 (2002)]. Under the effect of hypoxia (e.g. culturing in the presence of 1% oxygen for 24 hours) or under the action of non-selective dioxygenase inhibitors (e.g. desferroxamine in a concentration of 100 µM, cobalt chloride in a concentration of 100 µM or N-oxalylglycine diethyl ester in a concentration of 1 mM), the test cell line produces luciferase, which can be detected and quantified with the aid of suitable bioluminescence reagents (e.g. Steady-Glo® Luciferase Assay System, Promega Corporation, Madison, Wis. 53711, USA) and a suitable luminometer.

Test procedure: On the day before the test, the cells are plated out in an exactly calculated amount of culture medium (DMEM, 10% FCS, 2 mM glutamine) in 384- or 1,536-well microtiter plates and kept in a cell incubator (96% atmospheric humidity, 5% v/v $CO_2$, 37° C.). On the test day, the test substances are added to the culture medium in graduated concentrations. No test substance is added to the cells in batches serving as negative controls. As a positive control for determination of the sensitivity of the cell to inhibitors, e.g. desferroxamine is added in a final concentration of 100 µM. Six to 24 hours after transfer of the test substances into the wells of the microtiter plates, the resulting light signal is measured in the luminometer. A dose/effect relationship is plotted with the aid of the measurement values, which serves as a basis for determining the half-maximum active concentration (called the $EC_{50}$ value).

1.c) Cellular, Functional In Vitro Test of Modification of the Gene Expression:

To investigate the modification of the expression of specific mRNAs in human cell lines after treatment with test substances, the following cell lines are cultured on 6- or 24-well plates: human hepatoma cells (HUH, JCRB Cell Bank, Japan), human embryonal kidney fibroblasts (HEK/293, ATCC, Manassas, Va. 20108, USA), human cervical carcinoma cells (HeLa, ATCC, Manassas, Va. 20108, USA), human umbilical vein endothelial cells (HUVEC, Cambrex, East Rutherford, N.J. 07073, USA). 24 hours after addition of the test substances, the cells are washed with phosphate-buffered saline and the total RNA is obtained from them using a suitable method (e.g. Trizol® reagent, Invitrogen GmbH, 76131 Karlsruhe, Germany).

For a typical analysis experiment, 1 µg each of the total RNA obtained in this way is digested with DNase I and translated into a complementary DNA (cDNA) using a suitable reverse transcriptase reaction (ImProm-II Reverse Transcription System, Promega Corporation, Madison, Wis. 53711, USA). 2.5% of the cDNA batch obtained in this way is used in each case for the polymerase chain reaction. The expression level of the mRNA of the genes to be investigated is investigated by means of the real time quantitative polymerase chain reaction [TaqMan-PCR; Heid C. A., Stevens J., Livak K. J., Williams P. M., *Genome Res.* 6 (10), 986-94 (1996)] using an ABI Prism 7700 sequence detection instrument (Applied Biosystems, Inc.). The primer-probe combinations used here are generated by means of Primer Express 1.5 Software (Applied Biosystems, Inc.). Specifically, the mRNAs of erythropoietin, carboanhydrase IX, lactate dehydrogenase A and vascular endothelial cell growth factor are investigated.

Substances according to the present invention lead to a significant dose-dependent increase in the mRNA of hypoxia-induced genes in cells of human origin.

2. In Vivo Tests for Detection of the Action in the Cardiovascular System 2.a) In Vivo Test of Modification of Gene Expression:

The test compounds dissolved in suitable solvents are administered to mice or rats either orally by stomach tube administration, intraperitoneally or intravenously. Typical dosages are 0.1, 0.5, 1, 5, 10, 20, 50, 100 and 300 mg substance per kg of body weight and administration. Control animals receive only solvent. 4, 8 or 24 hours after administration of the test substance the animals are sacrificed with an overdose of isoflurane and a subsequent fracture of the neck and the organs to be investigated are removed. Parts of the organs are shock-frozen in liquid nitrogen. Total RNA is obtained from the organ parts as described under B.1.a) and this is translated into a cDNA. The expression level of the mRNA of the genes to be investigated is investigated by means of the real time quantitative polymerase chain reaction [TaqMan-PCR; Heid C. A., Stevens J., Livak K. J., Williams P. M., *Genome Res.* 6 (10), 986-94 (1996)] using an ABI Prism 7700 sequence detection instrument (Applied Biosystems, Inc.).

Substances according to the present invention lead to a significant dose-dependent increase in the mRNA of erythropoietin in the kidney after oral or parenteral administration compared with the placebo control.

2.b) Determination of the Erythropoietin Level in Serum:

The test substance in a suitable solvent is administered to mice or rats either intraperitoneally or orally once or twice daily. Typical dosages are 0.1, 0.5, 1, 5, 10, 20, 50, 100 and 300 mg substance per kg of body weight and administration. Placebo control animals receive only solvent. Before the administration and four hours after the last administration of substance, 50 µl of blood are taken from the animals from the retroorbital venous plexus or the tail vein under short narcosis. The blood is rendered uncoagulable by addition of lithium heparin. The blood plasma is obtained by centrifugation. The content of erythropoietin in the blood plasma is determined with the aid of an erythropoietin-ELISA (Quantikine® mouse Epo Immunoassay, R&D Systems, Inc., Minneapolis, USA) in accordance with the manufacturer's instructions. The measurement values are converted into pg/ml with the aid of a reference measurement recorded for mouse erythropoietin.

Substances according to the present invention lead to a significant dose-dependent increase in the plasma erythropoietin after oral and parental administration compared with the starting value and the placebo control.

2.c) Determination of the Cell Composition of Peripheral Blood:

The test substance in a suitable solvent is administered to mice or rats either intraperitoneally or orally once or twice daily for several days. Typical dosages are e.g. 0.1, 0.5, 1, 5, 10, 20, 50, 100 and 300 mg substance per kg of body weight and administration. Control animals receive only solvent. At the end of the study, blood is taken from the animals from the venous plexus of the corner of the eye or the tail vein under short narcosis and is rendered uncoagulable by addition of sodium citrate. The concentrations of erythrocytes, leukocytes and thrombocytes are determined in the blood samples in a suitable electronic measuring apparatus. The concentration of the reticulocytes is determined by microscope screening of in each case 1000 erythrocytes with the aid of blood smears stained with a stain solution suitable for this purpose (KABE Labortechnik, Nümbrecht). For determination of the haematocrit, blood is taken from the retroorbital venous plexus by means of a haematocrit capillary and the haematocrit value is read off manually after centrifugation of the capillary in a centrifuge suitable for this purpose.

Substances according to the present invention lead to a significant dose-dependent increase in the haematocrit, the erythrocyte count and the reticulocytes after oral and parenteral administration compared with the starting value and the placebo control.

3. Determination of the Solubility

Preparation of the Starting Solution (Initial Solution):

At least 1.5 mg of the test substance are weighed out accurately into a Wide Mouth 10 mm Screw V-Vial (from Glastechnik Grädfenroda GmbH, Art. No. 8004-WM-H/V15µ) with fitting screw cap and septum, DMSO is added to give a concentration of 50 mg/ml and the mixture is vortexed for 30 minutes.

Preparation of the Calibration Solutions:

The required pipetting steps are carried out in a 1.2 ml Deep Well Plate (DWP) with 96 wells using a liquid handling robot. The solvent used is a mixture of acetonitrile/water 8:2.

Preparation of the starting solution for calibration solutions (stock solution): 833 µl of the solvent mixture are added to 10 µl of the initial solution (concentration=600 µg/ml), and the mixture is homogenized. For each test substance, 1:100 dilutions are prepared in separate DWPs, and the dilutions for their part are homogenized.

Calibration solution 5 (600 ng/ml): 270 µl of solvent mixture are added to 30 µl of the stock solution, and the mixture is homogenized.

Calibration solution 4 (60 ng/ml): 270 µl of solvent mixture are added to 30 µl of calibration solution 5, and the mixture is homogenized.

Calibration solution 3 (12 ng/ml): 400 µl of solvent mixture are added to 100 µl of calibration solution 4, and the mixture is homogenized.

Calibration solution 2 (1.2 ng/ml): 270 µl of solvent mixture are added to 30 µl of calibration solution 3, and the mixture is homogenized.

Calibration solution 1 (0.6 ng/ml): 150 µl of solvent mixture are added to 150 µl of calibration solution 2, and the mixture is homogenized.

Preparation of the Sample Solutions:

The required pipetting steps are carried out in a 1.2 ml DWP with 96 wells using a liquid handling robot. 1000 µl of PBS buffer pH 6.5 are added to 10.1 µl of the stock solution. (PBS buffer pH 6.5: 61.86 g of sodium chloride, 39.54 g of sodium dihydrogen phosphate and 83.35 g of 1 N aqueous sodium hydroxide solution are weighed out into a 1 litre measuring flask, the flask is filled with water and the mixture is stirred for about 1 hour. From this solution, 500 ml are added to a 5-litre measuring flask, and the flask is filled with water. Using 1 N aqueous sodium hydroxide solution, the pH is adjusted to 6.5.)

Practice:

The required pipetting steps are carried out in a 1.2 ml DWP with 96 wells using a liquid handling robot. Using a temperature-adjustable shaker, the sample solutions prepared in this manner are shaken at 20° C. and 1400 rpm for 24 hours. From these solutions, in each case 180 µl are removed and transferred into Beckman polyallomer centrifuge tubes. These solutions are centrifuged at about 223 000×g for 1 hour. From each sample solution, 100 µl of the supernatant are removed and diluted 1:10 and 1:1000 with PBS buffer 6.5.

Analysis:

The samples are analyzed by HPLC/MS-MS. Quantification is carried out using a five-point calibration curve of the test compound. The solubility is expressed in mg/l. Analysis sequence: 1) blank (solvent mixture); 2) calibration solution 0.6 ng/ml; 3) calibration solution 1.2 ng/ml; 4) calibration solution 12 ng/ml; 5) calibration solution 60 ng/ml; 6) calibration solution 600 ng/ml; 7) blank (solvent mixture); 8) sample solution 1:1000; 7) sample solution 1:10.

HPLC/MS-MS Method

HPLC: Agilent 1100, quat. pump (G1311A), autosampler CTC HTS PAL, degasser (G1322A) and column thermostat (G1316A); column: Oasis HLB 20 mm×2.1 mm, 25 p; temperature: 40° C.; mobile phase A: water+0.5 ml of formic acid/l; mobile phase B: acetonitrile+0.5 ml of formic acid/l; flow rate: 2.5 ml/min; stop time 1.5 mm; gradient: 0 mm 95% A, 5% B; ramp: 0-0.5 mm 5% A, 95% B; 0.5-0.84 min 5% A, 95% B; ramp: 0.84-0.85 min 95% A, 5% B; 0.85-1.5 min 95% A, 5% B.

MS/MS: WATERS Quattro Micro Tandem MS/MS; Z-Spray API interface; HPLC-MS initial splitter 1:20; measurement in the ESI mode.

C. Embodiment Examples for Pharmaceutical Compositions

The compounds according to the invention can be converted into pharmaceutical formulations as follows:

Tablet:

Composition:

100 mg of the compound according to the invention, 50 mg lactose (monohydrate), 50 mg maize starch (native), 10 mg polyvinylpyrrolidone (PVP 25) (BASF, Ludwigshafen, Germany) and 2 mg magnesium stearate.

Tablet weight 212 mg. Diameter 8 mm, radius of curvature 12 mm.

Preparation:

The mixture of compound according to the invention, lactose and starch is granulated with a 5% strength solution (w/w) of the PVP in water. After drying, the granules are mixed with the magnesium stearate for 5 minutes. This mixture is pressed with a conventional tablet press (for tablet format see above). A pressing force of 15 kN is used as the recommended value for the pressing.

Suspension for Oral Administration:

Composition:

1000 mg of the compound according to the invention, 1000 mg ethanol (96%), 400 mg Rhodigel® (xanthan gum from FMC, Pennsylvania, USA) and 99 g water.

10 ml of oral suspension correspond to an individual dose of 100 mg of the compound according to the invention.

Preparation:

The Rhodigel is suspended in ethanol and the compound according to the invention is added to the suspension. The water is added with stirring. The mixture is stirred for approx. 6 h until swelling of the Rhodigel has ended.

Solution for Oral Administration:

Composition:

500 mg of the compound according to the invention, 2.5 g polysorbate and 97 g polyethylene glycol 400.20 g of oral solution correspond to an individual dose of 100 mg of the compound according to the invention.

Preparation:

The compound according to the invention is suspended in a mixture of polyethylene glycol and polysorbate, while stirring. The stirring operation is continued until dissolution of the compound according to the invention is complete.

i.v. Solution:

The compound according to the invention is dissolved in a concentration below the saturation solubility in a physiologically acceptable solvent (e.g. isotonic saline solution, glucose solution 5% and/or PEG 400 solution 30%). The solution is subjected to sterile filtration and is transferred into sterile and pyrogen-free injection containers.

What is claimed is:

1. A compound of the formula

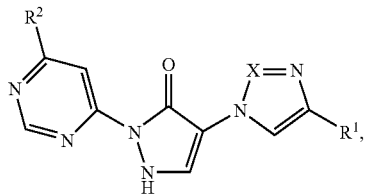   (I)

in which
X represents N or CH;
$R^1$ represents hydrogen or cyano; and
$R^2$ represents a saturated 4- to 7-membered heterocyclyl radical which is attached via a nitrogen atom,
where the heterocyclyl radical may be substituted by a substituent, where the substituent is selected from the group consisting of hydroxyl, hydroxycarbonyl, $C_1$-$C_3$-alkyl, $C_1$-$C_3$-alkylamino and $C_3$-$C_6$-cycloalkyl,
or
where the heterocyclyl radical may be substituted by 1 to 4 fluorine substituents, or a salt thereof.

2. A compound according to claim 1, wherein
X represents N or CH;
$R^1$ represents hydrogen or cyano; and
$R^2$ represents a saturated 4- to 7-membered heterocyclyl radical which is attached via a nitrogen atom,
where the heterocyclyl radical is substituted by 1 to 4 fluorine substituents,
or
$R^2$ represents piperazin-1-yl,
where piperazin-1-yl is substituted by one substituent, where the substituent is selected from the group consisting of $C_3$-$C_6$-cycloalkyl,
or
$R^2$ represents azetidin-1-yl,
where azetidin-1-yl is substituted by one substituent, where the substituent is selected from the group consisting of hydroxycarbonyl, $C_1$-$C_3$-alkyl, $C_1$-$C_3$-alkylamino and $C_3$-$C_6$-cycloalkyl,
or
$R^2$ represents 1,2-oxazinan-2-yl or 1,4-oxazepan-4-yl,
or a salt thereof.

3. A compound according to claim 1, wherein
X represents N or CH;
$R^1$ represents hydrogen or cyano; and
$R^2$ represents azetidin-1-yl, pyrrolin-1-yl or piperidin-1-yl,
where azetidin-1-yl, pyrrolin-1-yl and piperidin-1-yl are substituted by 1 to 4 fluorine substituents,
or
$R^2$ represents piperazin-1-yl,
where piperazin-1-yl is substituted in the 4-position by one substituent, where the substituent is selected from the group consisting of $C_3$-$C_6$-cycloalkyl,
or
$R^2$ represents azetidin-1-yl,
where azetidin-1-yl is substituted in the 3-position by one substituent, where the substituent is selected from the group consisting of hydroxycarbonyl, methyl and dimethylamino,
or
$R^2$ represents 1,2-oxazinan-2-yl or 1,4-oxazepan-4-yl,
or a salt thereof.

4. A method for preparing a compound of the formula (I) or a salt thereof according to claim 1, wherein
[A] a compound of the formula

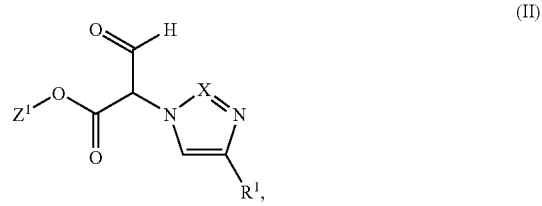   (II)

in which $R^1$ has the meaning given in claim 1, and
$Z^1$ represents methyl or ethyl,
is reacted in an inert solvent, if appropriate in the presence of an acid, with a compound of the formula

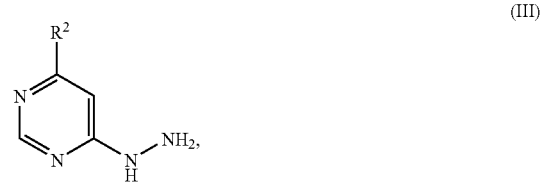   (III)

in which $R^2$ has the meaning given in claim 1,
to give a compound of the formula

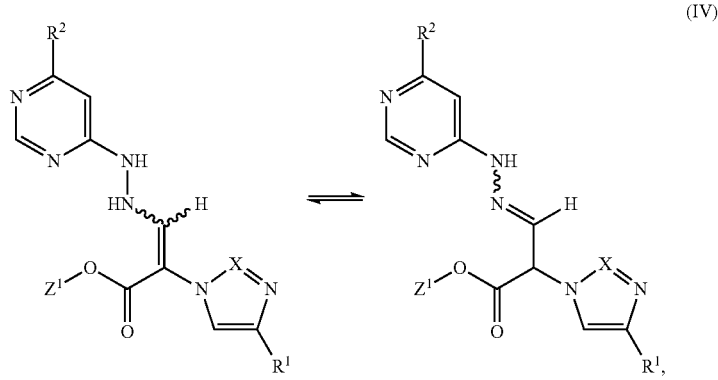   (IV)

in which $Z^1$, $R^1$ and $R^2$ have the meaning given in claim 1, which, already under these reaction conditions or in a subsequent reaction step under the influence of a base, cyclizes to give the compound of the formula (I), and the compound of the formula (I) is, if appropriate with the appropriate (i) solvent and/or (ii) base or acid, converted into one of its salts, or

[B] a compound of the formula

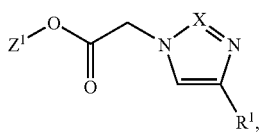

(V)

in which $Z^1$ and $R^1$ have the meaning given in claim 1, is condensed with a compound of the formula

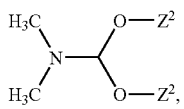

(VI)

in which
$Z^2$ represents methyl or ethyl,
to give a compound of the formula

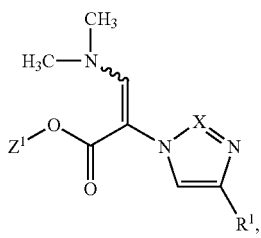

(VII)

in which $Z^1$ and $R^1$ have the meaning given in claim 1, and then reacted in the presence of an acid with a compound of the formula (III) to give a compound of the formula (IV), which, already under these reaction conditions or in a subsequent reaction step under the influence of a base, cyclizes to give the compound of the formula (I), and the compound of the formula (I) is, if appropriate with the appropriate (i) solvent and/or (ii) base or acid, converted into one of its salts, or

[C] the compound of the formula

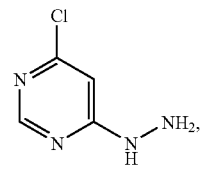

(VIII)

is, in water as the solvent in a one-pot process, reacted initially with a compound of the formula $R^1$—H     (IX), in which $R^2$ has the meaning given in claim 1, and then with a compound of the formula (VII) to give a compound of the formula (I), and the compound of the formula (I) is, if appropriate with the appropriate (i) solvent and/or (ii) base or acid, converted into one of its salts.

5. A pharmaceutical composition comprising a compound according to claim 1 in combination with an inert, non-toxic, pharmaceutically acceptable excipient.

6. A method for treating anemia in a subject comprising administering a therapeutically effective amount of a compound according to claim 1.

7. A compound according to claim 1, characterized in that
X represents N or CH,
$R^1$ represents hydrogen or cyano, and
$R^2$ represents piperazin-1-yl,
wherein piperazin-1-yl is substituted by a substituent selected from the group consisting of $C_3$-$C_6$-cycloalkyl,
or a salt thereof.

8. A compound according to claim 7, characterized in that
X represents N or CH,
$R^1$ represents hydrogen or cyano, and
$R^2$ represents piperazin-1-yl,
wherein piperazin-1-yl is substituted in the 4-position by a substituent selected from the group consisting of $C_3$-$C_6$-cycloalkyl,
or a salt thereof.

9. A compound according to claim 1, characterized in that
X represents N or CH,
$R^1$ represents hydrogen or cyano, and
$R^2$ represents azetidin-1-yl,
wherein azetidin-1-yl is substituted by a substituent selected from the group consisting of hydroxycarbonyl, $C_1$-$C_3$-alkyl, $C_1$-$C_3$-alkylamino and $C_3$-$C_6$-cycloalkyl,
or a salt thereof.

10. A compound according to claim 9, characterized in that
X represents N or CH,
$R^1$ represents hydrogen or cyano, and
$R^2$ represents azetidin-1-yl,
wherein azetidin-1-yl is substituted by a substituent selected from the group consisting of hydroxycarbonyl, methyl and dimethylamino,
or a salt thereof.

11. A compound according to claim 10, characterized in that
X represents N or CH,
$R^1$ represents hydrogen or cyano, and
$R^2$ represents azetidin-1-yl,
wherein azetidin-1-yl is substituted in the 3-position by a substituent selected from the group consisting of hydroxycarbonyl, methyl and dimethylamino,
or a salt thereof.

12. A compound according to claim 1, characterized in that

X represents N or CH,

R[1] represents hydrogen or cyano, and

R[2] represents 1,2-oxazinan-2-yl or 1,4-oxazepan-4-yl, or a salt thereof.

13. A compound according to claim 1, wherein R[2] represents 4-cyclobutyl-piperazin-1-yl.

14. A compound according to claim 1, wherein the compound is 1-{2-[6-(4-Cyclobutylpiperazin-1-yl)pyrimidin-4-yl]-3-oxo-2,3-dihydro-1H-pyrazol-4-yl}-1H-imidazole-4-carbonitrile, as represented by the formula

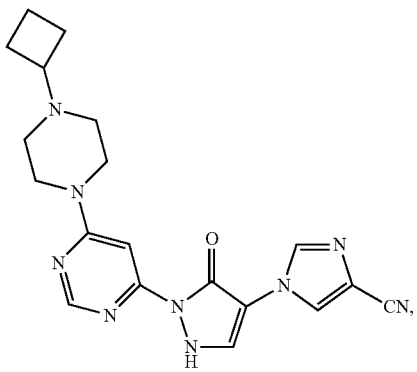

or a salt thereof.

15. A compound according to claim 1, where the compound is 1-{2-[6-(4-Cyclobutylpiperazin-1-yl)pyrimidin-4-yl]-3-oxo-2,3-dihydro-1H-pyrazol-4-yl}-1H-imidazole-4-carbonitrile, as represented by the formula

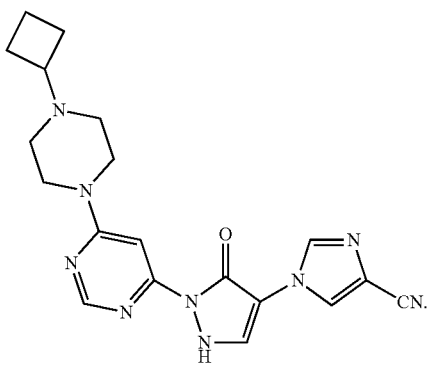

16. A compound according to claim 1, where the compound is 1-{6-[5-Oxo-4-(1H-1,2,3-triazol-1-yl)-2,5-dihydro-1H-pyrazol-1-yl]pyrimidin-4-yl}azetidine-3-carboxylic acid, as represented by the formula

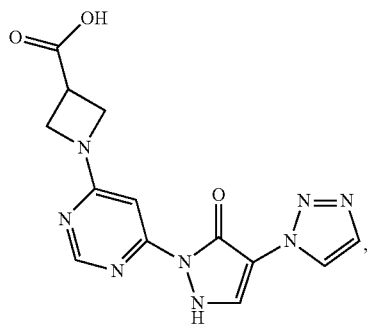

or a salt thereof.

17. A compound according to claim 1, where the compound is 1-{6-[5-Oxo-4-(1H-1,2,3-triazol-1-yl)-2,5-dihydro-1H-pyrazol-1-yl]pyrimidin-4-yl}azetidine-3-carboxylic acid, as represented by the formula

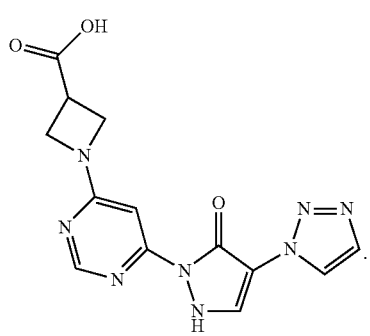

18. A compound according to claim 1, where the compound is 2-[6-(1,2-Oxazinan-2-yl) pyrimidin-4-yl]-4-(1H-1,2,3-triazol-1-yl)-1,2-dihydro-3H-pyrazol-3-one, as represented by the formula

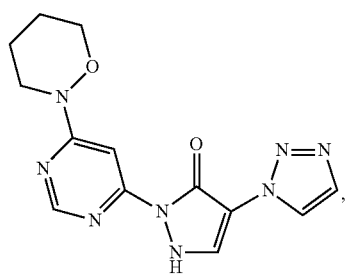

or a salt thereof.

19. A compound according to claim 1, where the compound is 2-[6-(1,2-Oxazinan-2-yl) pyrimidin-4-yl]-4-(1H-1,2,3-triazol-1-yl)-1,2-dihydro-3H-pyrazol-3-one, as represented by the formula

20. A compound according to claim 1, where the compound is 1-{2-[6-(1,2-Oxazinan-2-yl)pyrimidin-4-yl]-3-oxo-2,3-dihydro-1H-pyrazol-4-yl}-1H-1,2,3-triazole-4-carbonitrile, as represented by the formula:
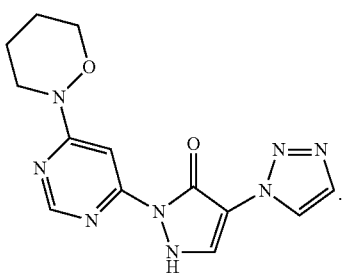
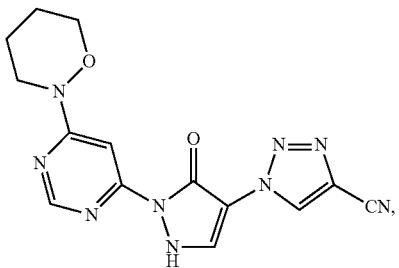
or a salt thereof.
21. A compound according to claim 1, wherein the compound is 1-{2-[6-(1,2-Oxazinan-2-yl)pyrimidin-4-yl]-3-oxo-2,3-dihydro-1H-pyrazol-4-yl}-1H-1,2,3-triazole-4-carbonitrile, as represented by the formula:
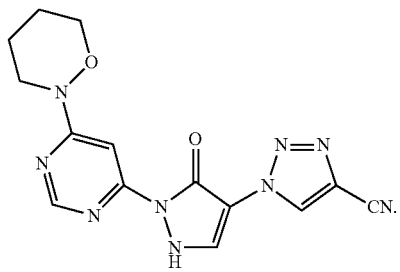
* * * * *